US008863585B2

(12) United States Patent
Wang et al.

(10) Patent No.: US 8,863,585 B2
(45) Date of Patent: Oct. 21, 2014

(54) REVERSAL BENDING FATIGUE TESTING

(75) Inventors: Jy-An John Wang, Oak Ridge, TN (US); Hong Wang, Oak Ridge, TN (US); Ting Tan, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 278 days.

(21) Appl. No.: 13/396,413

(22) Filed: Feb. 14, 2012

(65) Prior Publication Data
US 2013/0205911 A1   Aug. 15, 2013

(51) Int. Cl.
*G01N 3/32*   (2006.01)
(52) U.S. Cl.
USPC .......................................................... 73/812
(58) Field of Classification Search
CPC ........................................................ G01N 3/32
USPC ................................................. 73/812, 856
See application file for complete search history.

(56) References Cited

U.S. PATENT DOCUMENTS

| 5,231,882 A | 8/1993 | Bertele et al. |
| 6,931,942 B2 | 8/2005 | Uhlik et al. |
| 7,690,265 B2 | 4/2010 | Cipra |

OTHER PUBLICATIONS

Gross, "Engineering Materials Evaluation by Reversed Bending," *Manual on Low Cycle Fatigue Testing, ASTM STP 465*, ASTM, Philadelphia, pp. 149-162, (1969).
ASTM E-9 Committee on Fatigue, Handbook of Fatigue Testing, ASMT STP 566, Ed. S. R. Swanson, ASTM, Philadelphia, pp. 19-84, (1974).
Jhansale et al., "Equipment for cyclic deformation and fatigue studies in pure bending," SESA Fall Meeting, Society for Experimental Stress Analysis, Boston, MA, Oct. 18-22, Paper No. 1726. (1970).
Ghamian, et al., "Inelastic Deformations of Mild-steel Beams Under Symmetrical and Unsymmetrical Cyclic Bending," *Experimental Mechanics*, pp. 49-56 (1974).
Monismith, et al. "Fatigue of Asphalt Paving Mixtures," *Transportation Engineering Journal*, pp. 317-346 (1969).
Tayebali, et al., "Development and Evaluation of Dynamic Flexural Beam Fatigue Test System," *Transportation Research Record 1545*, Transportation Research Board, Washington, D.C., pp. 89-97 (1996).
Abojaradeh, et al., "Validation of Initial and Failure Stiffness Definition in Flexure Fatigue Test for Hot Mix Asphalt," *Journal of Testing and Evaluation*, 35(1):1-8 (2007).
Adsit et al., "Flexure Fatigue Testing of Titanium Forging Material in Liquid Hydrogen," *Fatigue and Fracture Toughness—Cryogenic Behavior, ASTM STP*, 556:44-54 (1974).
Artamendi et al., "Characterization of fatigue damage for paving asphaltic materials," *Fatigue Fract Engng Mater Struct*, 28:1113-1118 (2005).
ASTM C1161-94, "Standard Test Method for Flexure Strength of Advanced Ceramics at Ambient Temperature," ASTM International, pp. 1-7 (1994).

(Continued)

*Primary Examiner* — Lisa Caputo
*Assistant Examiner* — Brandi N Hopkins
(74) *Attorney, Agent, or Firm* — Klarquist Sparkman, LLP

(57) ABSTRACT

Embodiments for apparatuses for testing reversal bending fatigue in an elongated beam are disclosed. Embodiments are configured to be coupled to first and second end portions of the beam and to apply a bending moment to the beam and create a pure bending condition in an intermediate portion of the beam. Embodiments are further configured to cyclically alternate the direction of the bending moment applied to the beam such that the intermediate portion of the beam cyclically bends in opposite directions in a pure bending condition.

15 Claims, 16 Drawing Sheets

(56) References Cited

OTHER PUBLICATIONS

ASTM B 593-96, "Standard Test Method for Bending Fatigue Testing for Copper-Alloy Spring Materials," *ASTM International*, 5 pp. (2009).

Batte et al., "Reverse-bend Testing to Obtain Long-term Endurance Data," *Techniques for High Temperature Fatigue Testing*, pp. 97-115 (1985).

Bowman, "End Constraint and Alignment Effects in Three and Four Point Tension-Compression Bending Tests," *MTS Systems Corporation*, Minneapolis, MN, 9 pp. (1989).

Carden, "Fatigue at Elevated Temperatures: a Review of Test Methods," *Fatigue at Elevated Temperatures, ASTM STP*, 520:195-223 (1973).

DePaul et al., "Some Microstructural and Alloying Effects Upon Low-Cycle Fatigue Life of Pressure Vessel Steels," *Fatigue at High Temperature, ASTM STP*, 459: 130-143 (1969).

Forrest et al., "New Approach to Thermal Fatigue Testing," *Engineering*, 192:522-523 (1961).

Gao, et al., An effective method to investigating short crack growth behavior by reverse bending testing,: *International Journal of Fatigue*, 29:565-574 (2007).

Gross, et al., "Factors Affecting Resistance of Pressure Vessel Steels to Repeated Overloading," *Fatigue of Steels*, 32(1):23-s-30-s, (1953).

Hartman et al., "Evaluating Four-Point Bend Fatigue of Asphalt Mix Using Image Analysis," *Journal of Materials in Civil Engineering*, 16(1):60-68 (2004).

IPC Global, "Servo-pneumatic Four Point Bending Apparatus," www.ipcglobal.com.au, 2 pp. (2010).

Jiang et al., "Effects of shot-peening and re-shot-peening on four-point bend fatigue behavior of Ti-6Al-4V," *Materials Science &Engineering A*, 468-470:137-143 (2007).

Lagneborg et al., The Effect of Combined Low-Cycle Fatigue and Creep on the Life of Austenitic Stainless Steels, *Metallurgical Transactions*, 2:1821-1827 (1971).

Li et al., "Four-Point-Bend Fatigue of AA 2026 Aluminum Alloys," *Metallurgical and Materials Transactions A*, 36A:2529-2539 (2005).

Morrison et al., "Four-point-bending-fatigue behavior of the Zr-based Vitreloy 105 bulk metallic glass," *Materials Science &Engineering A*, 467:190-197 (2007).

O'Brien et al., "Transverse tension fatigue life characterization through flexure testing of composite materials," *International Journal of Fatigue*, 24:127-145 (2002).

Tor et al., "Repeated Load Tests on Welded and Prestrained Steels," *Welding Research Supplement*, 31(5):238-s-246-s (1952).

Weibull, "Fatigue Testing and Analysis of Results" and "Fatigue Testing Machines and Equipment," Pergamon Press, New York, pp. 31-65 (1961).

White, "Effect of Environment and Hold Time on the High Strain Fatigue Endurance of 1/2 Per Cent Molybdenum Steel," *Proc. Instn. Mech. Engrs.*, 184(1):223-240 (1969-70).

White et al., "Strain Concentration in Beams Under Cyclic Plastic Straining," *Journal of Strain Analysis*, 3 (4):313-324 (1968).

Zhai et al., "A self-aligning four-point bend testing rig and sample geometry effect in four-point bend fatigue," *International Journal of Fatigue*, 21:889-894 (1999).

Zhai et al., "The grain boundary geometry for optimum resistance to growth of short fatigue cracks in high strength Al-alloys," *International Journal of Fatigue*, 27:1202-1209 (2005).

Zhang et al., "Distributions of pore size and fatigue weak link strength in an A713 sand cast aluminum alloy,", *Materials Science &Engineering A*, 527:3639-3644 (2010).

Zineb et al., "An original pure bending device with large displacements and rotations for static and fatigue tests of composite structures," *Composites Part B: Engineering*, 34:447-458 (2003).

REVERSAL BENDING FATIGUE TESTING

ACKNOWLEDGMENT OF GOVERNMENT SUPPORT

This invention was made with government support under Contract No. DE-AC05-00OR22725 awarded by the U.S. Department of Energy. The government has certain rights in the invention.

FIELD

This disclosure is related to apparatuses and methods for testing reversal bending fatigue in a beam specimen, such as a spent nuclear fuel rod.

SUMMARY

Embodiments for testing reversal bending fatigue in an elongated beam are disclosed. Embodiments are configured to be coupled to first and second end portions of a beam and to apply a bending moment to the beam and create a pure bending condition in an intermediate portion of the beam while eliminating or reducing axial and shear stresses on the beam. Embodiments are further configured to cyclically alternate the direction of the bending moment applied to the beam such that the intermediate portion of the beam cyclically bends in opposite directions in a pure bending condition. For example, embodiments can simulate vibrational fatigue in spent nuclear fuel rods caused by vibration during transportation.

The foregoing and other objects, features, and advantages of the invention will become more apparent from the following detailed description, which proceeds with reference to the accompanying figures.

DETAILED DESCRIPTION

General Considerations

Figure 1:
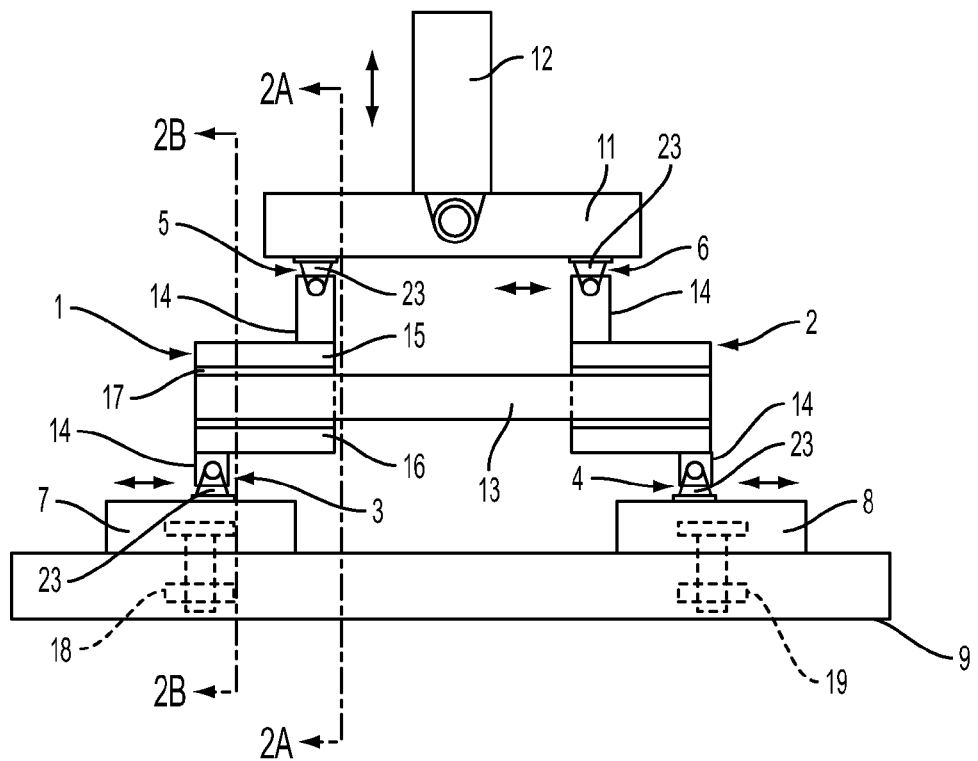
FIG. 1 is an elevation view of an exemplary apparatus for testing reversal bending fatigue in a horizontally oriented beam.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means mechanically, chemically, magnetically or otherwise physically coupled or linked and does not exclude the presence of intermediate elements between the coupled or associated items absent specific contrary language.

Reversal Bending Fatigue Testing

For high burn-up spent nuclear fuel (SNF), it is expected that the spent fuel cladding will have a high population of microcracks and hydrides, including macro-hydrides and micro-hydrides. This will reduce the stress intensity required to advance the crack growth. The linking of these microcracks during vibration loading can also reduce the fatigue threshold/incubation period significantly, accelerating fatigue failure. In addition to the damage in the cladding, the microstructure of fuel pellets and interfaces of fuel rods can change dramatically after the high burn-up process. These modifications and changes have a direct impact on the structural integrity and vibration response of SNF rods during transportation.

As a result, vibration has been included as a mandatory testing condition for the structural evaluation of a package that is used in transporting SNF by US NRE (United States Nuclear Regulatory Commission) in 10 CFR §71.71. Previously, a testing system was not available to test the SNF and evaluate the performance of fuel rods during transportation. Disclosed herein are exemplary apparatuses, systems, and methods that can be used, for example, for testing the response of a high burn-up SNF rod in a simulated loading condition.

In an exemplary transportation mode, SNF rods lie horizontally and are supported by spacers within a fuel rod support assembly. These rods are subjected to oscillatory bending, i.e. vibration, due to inertia effect. The vibration of a SNF rod during a transportation process typically features deflection rather than rotation or torsion, and the dominant frequencies involved with these dynamic events are generally less than 100 Hz. Accordingly, some embodiments disclosed herein are designed to simulate this repeated oscillatory bending of a rod-shaped specimen.

In addition to their typical composite structure of fuel pellets and cladding, SNF rods typically include various burn-induced damages (e.g., pores and micro cracks), oxide and hydride layers, residual stresses, altered interfaces, and trapped fissure products. More important, they are still highly radioactive after a long-term service in a nuclear reactor. These complications should preferably also be considered to more accurately test SNF rods. Accordingly, embodiments disclosed herein can be used to test specimens in very hostile and/or radioactive environments.

Exemplary Types of Bending

Bending testing can be primarily classified into cantilever beam bending, three-point bending, and four-point bending, according to the boundary conditions of a beam during testing.

Cantilever beam bending can have fewer boundary conditions to implement than other methods because one end of the beam is free. The support of the beam is usually stationary and the free end is typically driven by dedicated mechanisms. The bending moment in a loaded cantilever beam characteristically increases linearly over the length of specimen and this limits the failure in the local area near the support and furthers the sampling volume of specimen. As a result of that, the width of the specimen is usually made to decrease linearly so that a constant stress is produced over the larger part of a specimen.

Cantilever bending fatigue testing can be relatively straightforward to setup. But transverse shear exists over the whole length of the beam even if the specimen is setup horizontally or vertically. Generally, a guide roller joint can be used in the loading point for oscillatory motion at the free end. Axial forces can be easily introduced to the beam if the movement is restrained to a linkage.

Three-point bending and four-point bending have been traditionally used to test materials under quasi-static loading conditions. Though three-point bending can be simple to carry out, four-point bending is typically preferred because a larger volume of specimen material can be sampled. Traditional three-point and four-point bending testing is typically used with beams having a rectangular cross-section and the specimen is usually very sizable. Traditional three-point bending and four-point bending is further limited to small deflections of a beam and without bending reversal, as no restraint is typically provided to control motion of the beam in the direction opposite of the deflection direction.

In order to reduce or eliminate axial loading on a test beam in four-point bending, the testing apparatus can comprise connectors at the four loading points that allow the beam to move freely in the axial direction. The four loading points can be located on two specimen holding devices. Opposing end portions of the beam can be positioned within the holding devices and each of the holding devices can be subjected to a pair of offset loading contacts. Each holding device can convert an external force couple from the offset loading contacts into a bending moment applied to the respective end portion of the beam. Compliant layers can be employed as transits between rigid holding devices and the end portions of the beam to control potential contact damages.

The connectors at the contact points can be provided with pivot connections and/or slide connections such that the intermediate portion of the beam suspended between the two holding devices is subjected to a uniform bending moment with substantially no shear or axial stresses. The terms "pure bending" and "pure bending condition" are used herein to refer to this state of substantially uniform bending moment with substantially no shear or axial stresses. Pure bending conditions typically also include substantially no torsion stresses. Pure bending is a preferred condition for testing SNF rods as it closely simulates typical transportation conditions. Testing a beam in a pure bending condition can reduce irrelevant failure modes.

The set of connectors can have a large degree of flexibility and can allow the beam's ends to pivot and move axially, while at the same time can restrain the end portions of the beam from translating in the direction of deflection. This can allow the bending to be conducted in both forward and reverse modes, such as in an oscillating, or vibrational, pattern.

Several exemplary bending fatigue apparatuses and methods are disclosed herein for testing an elongated beam, such as high burn-up SNF rods or other specimens, with an intermediate portion of the beam under a pure bending condition.

Exemplary Horizontal Embodiments

FIG. 1 shows an exemplary apparatus for testing bending fatigue in a beam 13 under a reversal mode, with the beam positioned horizontally. The beam 13 comprises opposing first and second end portions and an intermediate portion between the first and second end portions, and defines a longitudinal axis extending between the first and second end portions. The apparatus is configured to apply opposing bending moments to the respective end portions of the beam while releasing axial forces on the beam in order to create a pure bending condition in the intermediate portion of the beam. The opposing bending moments are applied about moment axes that are generally perpendicular to the longitudinal axis of the beam (perpendicular to the page in FIG. 1). The bending moments cause the intermediate portion of the beam to deflect in an upward or downward direction that is generally perpendicular to the moment axes and the longitudinal axis of the beam.

The apparatus is further configured to cyclically alternate the direction of the resultant bending moment applied to the intermediate portion of the beam such that the intermediate portion of the beam cyclically deflects in opposite upward and downward directions while remaining in a pure bending condition.

The apparatus can comprise a pair of rigid sleeves 1, 2 for transferring the force couples from paired loading connections into the opposing end portions of the beam 13, creating the opposing bending moments. A compliant layer 17 can be sandwiched between the sleeves 1, 2 and the end portions of the beam 13, serving as buffer layers to limit contact-induced damage to the beam.

Connections 5, 6 can couple the sleeves 1, 2, respectively, to an overhead horizontal loading beam 11. Connection 3 can couple the sleeve 1 to a lower support plate 7, and connection 4 can couple the sleeve 2 to another lower support plate 8. The connections 3, 4, 5, 6 can allow the respective sleeves 1, 2 to pivot and translate axially relative to the loading beam 11 and the plates 7, 8, while at the same time restricting translation of the sleeves and the beam perpendicular to the axial direction of the beam. As used herein, the terms "translate" and "translation" have their ordinary meaning of movement from one position to another. A beam 13 with a circular section is used in this embodiment, but beams with other sectional shapes can also be used by modifying the shape of the sleeves 1, 2 to fit the shape of the beam. Other beams such as that with a rectangular section can be used equivalently. In addition, beams of any material type can be used.

Plates 7, 8 plates can be secured to a rigid base 9, such as via bolt sets 18 and 19. On the top, the loading beam 11 can be coupled to and driven by a force introducing mechanism, or loading rod, 12.

Figure 2A:
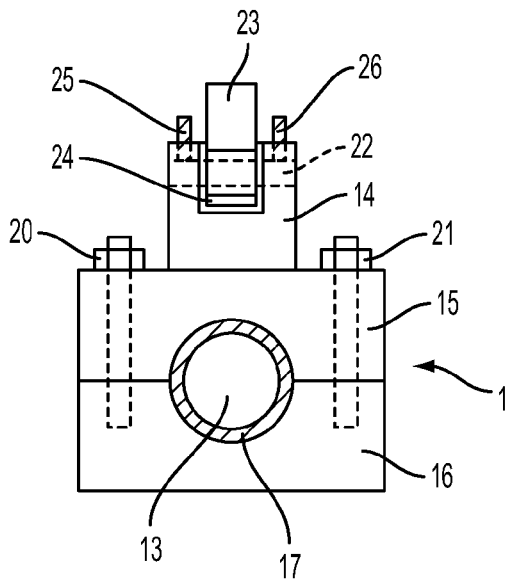
FIG. 2A is a partial cross-sectional view of the apparatus of FIG. 1, taken along section line 2A-2A of FIG. 1.
Figure 2B:
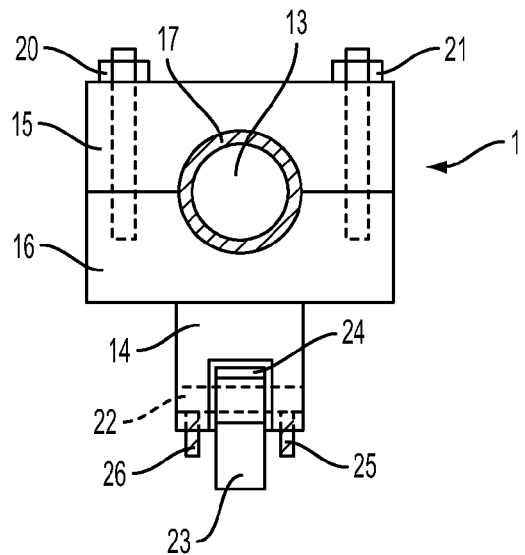
FIG. 2B is a partial cross-sectional view of the apparatus of FIG. 1, taken along section line 2B-2B of FIG. 1.

FIG. 2A is a partial cross-sectional view taken along line 2A-2A of FIG. 1, showing the portions of the rigid sleeves 1, 2 (for a beam 13 with a round section) that are coupled to the upper connections 5, 6. FIG. 2B is a partial cross-sectional view taken along line 2B-2B of FIG. 1, showing the portion of the sleeves 1, 2 coupled to the lower connections 3, 4. As shown in FIG. 2A, the sleeves 1, 2 can comprise a vertical part 14 and horizontal parts 15, 16. The assembly of a sleeve with the beam can include mounting a split compliant layer 16 and two halves 15, 16 of the rigid sleeve onto the end portion of the beam 13 and then clamping with bolt sets 20, 21. The vertical part 14 of the sleeve is fixedly integrated with the horizontal part 15 and pivoted with the plate 23, such as via a precision bearing 24. As shown, the plate 23 can be generally triangular. A roller 22 can be fixed to the rigid sleeve with set screws 25, 26 such that the roller can rotate with the sleeve within the bearing 24 relative to the plate 23. The use of high precision bearings 24 in the connections can reduce or eliminate backlash during reverse bending. The term "backlash" refers to a delay in force transfer through a connection due to a loose fitting such that one piece of the connection can move a small amount before being restricted by the other piece of the connection. Such a loose connection at any of the interfaces in the disclosed embodiments can cause delays in force transfer across the interface, particularly during oscillatory loading.

As shown in FIG. 2B, the sleeves 1, 2 can be coupled to the lower connections 3, 4 in substantially the same manner as the sleeves are coupled to the upper connections 5, 6, as described in FIG. 2A, but in an inversed orientation.

Figure 3A:
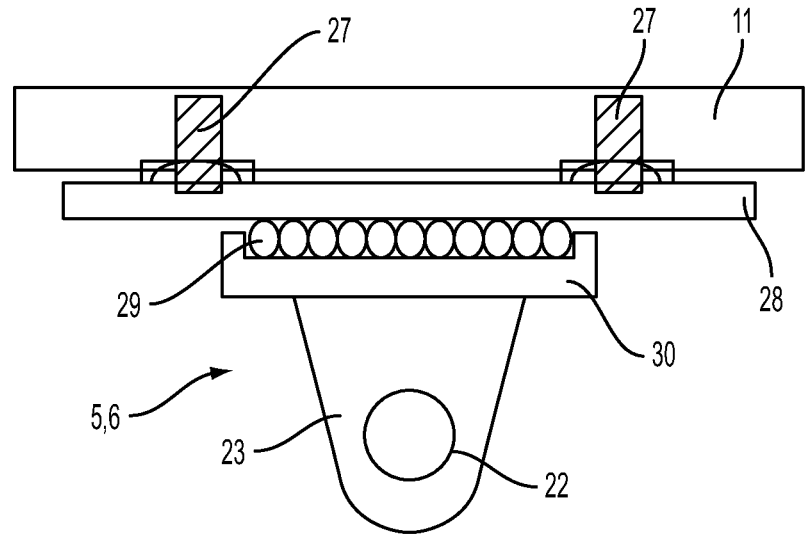
FIGS. 3A and 3B illustrate details of a pivot-slide connection of the apparatus of FIG. 1.
Figure 3B:
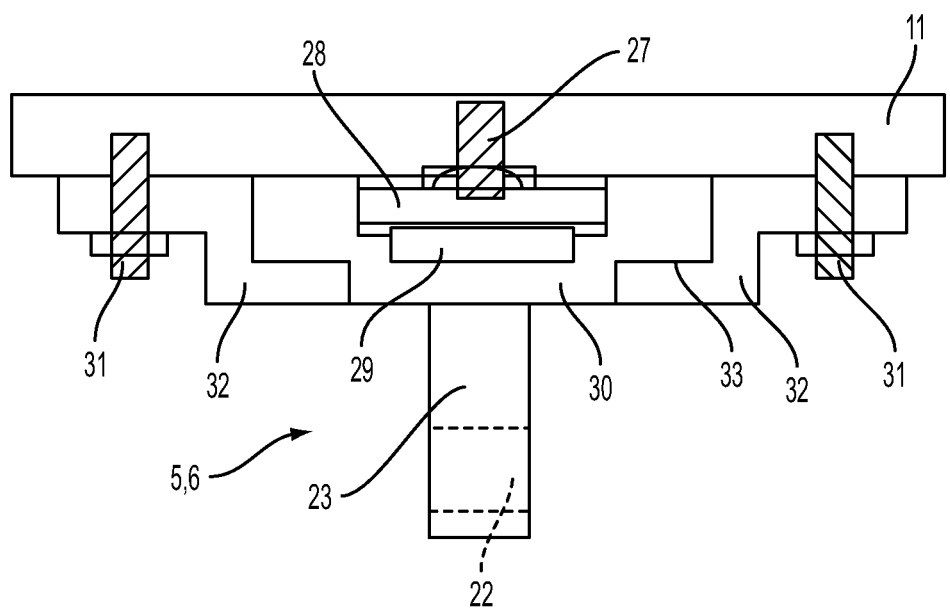

FIGS. 3A and 3B show additional details of the sliding capability of the upper connections 5, 6. The lower connections at 3, 4 can be constructed substantially the same, but in an inversed orientation. The upper connections 5, 6 can comprise a spring-loaded bolt set 27, a preloaded bearing track 28, a roller bearing, or other sliding bearing, 29, a retainer 30, a bolt set 31, and a mount 32. In the assembly of the connections, the roller bearing 29 and its retainer 30 can be placed and secured first through mount 32 by bolt set 31. The bolt set 27 can apply a preload on the bearing track 28. The magnitude of the preload can be based on the pressure requirement on the sliding interface 33. The sliding capability of the connections 5, 6 allow the plate 23 and the retainer 30, which are fixed together, to translate in the axial direction of the beam 13 relative to the track 28, the mount 32, and the loading beam 11, which are fixed together. The bearing 29 can comprise a plurality of ball bearings. The lower connections 3, 4 can comprise a similar construction as the upper connections 5, 6 in the coupling of the sleeves 1, 2 to the lower support plates 7, 8.

With the combination of the pivoting capability shown in FIGS. 2A and 2B with the sliding capability shown in FIGS. 3A and 3B, the connection 3, 4, 5, 6 can allow the sleeves 1, 2 and the beam 13 to freely pivot and translate axially relative to the loading beam 11 and the support plates 7, 8, and thereby release axial and shear loading on the beam in order to create a pure bending condition in the intermediate portion of the beam. At the same time, the connections 3, 4, 5, 6 can prevent the sleeves 1, 2 and the beam 13 from translating perpendicular to the axial direction of the beam.

In some embodiments, two of the connections 3, 4, 5, 6 can comprise the described pivoting and sliding connections while the other two of the connection can comprise only pivoting connections without the capability to slide axially if the pure bending condition is not compromised. For example, the upper two connections 5, 6 can comprise pivot-only connections, or the lower two connections 3, 4 can comprise pivot-only connections, or the left two connection 3, 5 can comprise pivot-only connections, or the right two connections 4, 6 can comprise pivot-only connections.

The support plates 7 and 8 and the associated lower connections 3, 4 can be calibrated and aligned with the upper loading beam 11 using a standard specimen prior to the routine testing (FIG. 1). A typical setup process for testing can begin with preparing the beam 13 with its ends encapsulated using the compliant layer 17. The prepared beam 13 can then be placed on the cylindrical surfaces of the lower halves 16 of rigid sleeves 1, 2 (FIG. 2B). The loading beam 11 with upper connections 5, 6 and the upper halves 15 of the sleeves 1, 2 can subsequently be lowered to a predetermined elevation so that the upper halves 15 match their counterpart lower halves 16. Bolt sets 20, 21 can then be applied to clamp the upper and lower halves of the sleeves.

Reversed bending of the beam 13 depends on the oscillatory movement of loading rod 12, as shown in FIG. 1. When the loading rod 12 is driven down, the push forces the left and right sleeves 1, 2 to rotate clockwise and counterclockwise, respectively. The corresponding bending moments make the intermediate portion of the testing beam 13 deflected downwards. On the other hand, an upwards deflection of the testing beam 13 occurs when the loading rod 12 is driven up.

The generated bending moments are related to the loading force and to the size of the sleeves 1, 2. Let the bending moment imparted on each of the end portions of the beam be M, let the applied concentrated force from the loading rod 12 be P, and let the horizontal length of the respective sleeve be L. Assuming that the tilt angle of the sleeve is sufficiently small so that its effect on the bending moment is negligible, then we have the following equation:

$$M = 0.5 * P * L. \tag{1A}$$

Figure 4:
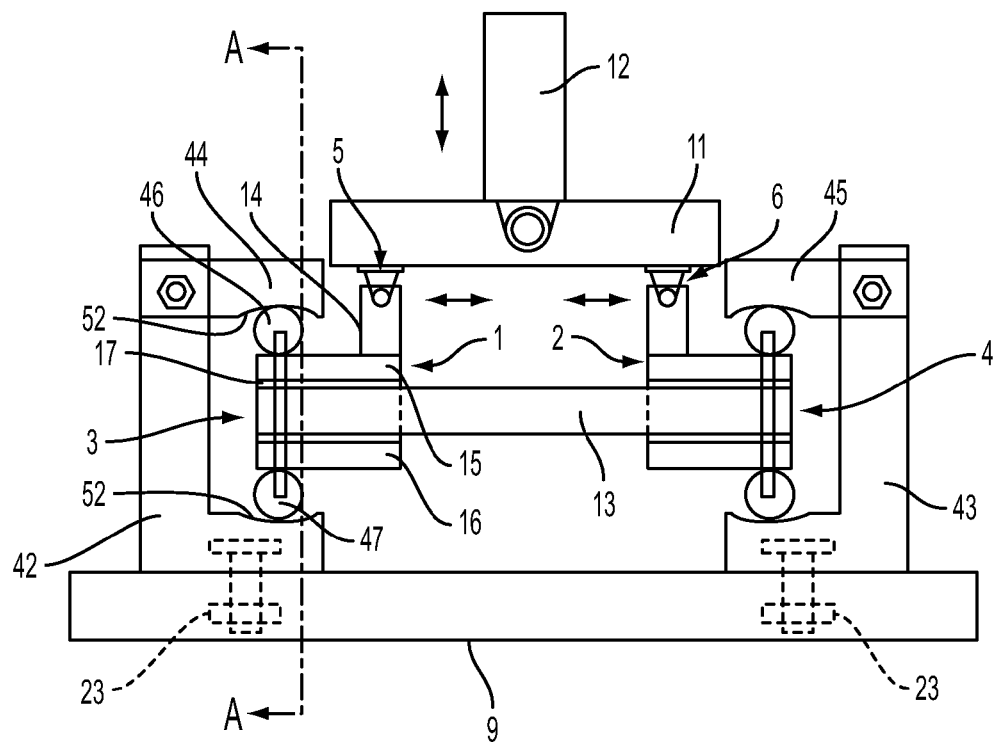
FIG. 4 is an elevation view of another exemplary apparatus for testing reversal bending fatigue in a horizontally oriented beam.
Figure 5:
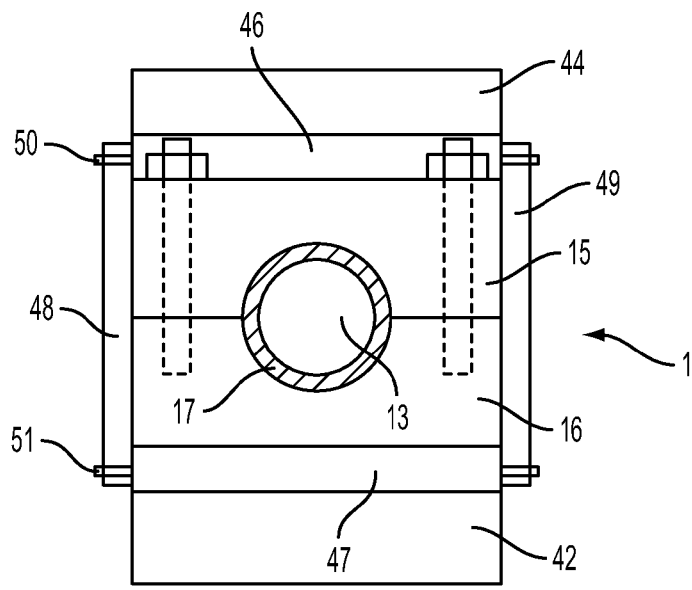
FIG. 5 is a cross-sectional view of the apparatus of FIG. 4, taken along section line A-A.

Another exemplary embodiment of a bending fatigue testing apparatus is shown in FIGS. 4 and 5. In this embodiment, the connections 3, 4 comprise rotary joints. Each rotary joint comprises a pair of cylindrical rollers 46, 47 positioned on opposite sides of the sleeves 1, 2. As shown, one of the rollers 46 is above the sleeve and the other roller 47 is below the sleeve. The rollers each have an axis of rotation that is generally parallel with the moment axis (perpendicular to the page in FIG. 4). The top roller 46 can be in contact with the top portion 15 of the sleeve and the bottom roller 47 can be in contact with the bottom portion 16 of the sleeve. Each pair of rollers 46, 47 can be coupled together by a pair of connecting rods 48, 49 that extend across the sides of the sleeves, as shown in FIG. 5. The rotary joints of connections 3, 4 can themselves be held in place by respective U-frame structures 42, 43. The U-frame structures 42, 43 can comprise curved, concave contact surfaces 52 at the top and bottom that serve as bearings for the rollers 46, 47. The elevation of the upper contact surfaces 52 can be adjustable through adjustable arms 44, 45. Rotation of rollers 46, 47 relative to the contact surfaces 52 results in rotation of the sleeves 1, 2 within the U-frames 42, 43, which can allow for both the rotation and the axial translation of rigid sleeves 1, 2 relative to the U-frames, releasing the axial forces that would otherwise be imparted to the intermediate portion of the beam 13. The upper connections 5, 6 that couple the loading beam 11 to the sleeves 1, 2 can have a similar construction as described above with reference to the embodiments of FIGS. 1-3.

As shown in FIG. 5, each of the connections 3, 4 is comprised of upper roller 46, lower roller 47, and connecting rods 48, 49. The rollers 46, 47 roll against the upper and lower surfaces of the rigid sleeves 1, 2 and roll against the concave bearing surfaces 52 of the U-frames 42, 43. Pins 50 and 51 can be used to mount the connecting rods 48, 49 to the axes of the upper and lower rollers 46, 47. As the loading rod 12 pushes downward, the left sleeve 1 rotates clockwise and the right sleeve 2 rotates counter-clockwise, causing the intermediate portion of the beam 13 to deflectdownward. As the sleeves 1, 2 rotate, the corresponding connecting rods 48, 49 rotate in the same direction and the corresponding rollers 46, 47 rotate in the opposite direction.

A standard specimen can be used to calibrate and align the position of the U-frames 42, 43 on the floor 9 of a host testing machine with the loading beam 11 prior to the routine setup of testing (FIG. 4). The beam 13 can then be made ready with its ends encapsulated using the compliant layer 17. With the lower rollers 47 and the lower halves 16 of sleeves 1, 2 placed on the respective lower bearing surfaces 52, the beam 13 can be lowered onto the cylindrical grooves of bottom halves 16 of the sleeves 1, 2. This can be followed by assembling the rest of the sleeves joints. The upper rollers 46, the connecting rods, 48, 49, and the upper aims 44, 45 of the U-frames 42, 43 can then be positioned and secured.

Reversed bending of the beam 13 can be performed by oscillatory movement of the loading rod 12. When the loading rod 12 moves down, the upper connections 5, 6 slide toward each other and the beam 13 is deflected downwards. When the loading rod 12 moves up, the upper connections 5, 6 slide away from each other and an upward deflection occurs in the beam 13. The rotation of the connections 3, 4 and the independent rotation of the rollers 46, 47 work together with the pivoting and sliding capabilities of the upper connections 5, 6, delivering an effective implementation of a pure bending load at the intermediate portion of the beam 13.

Figure 6A:
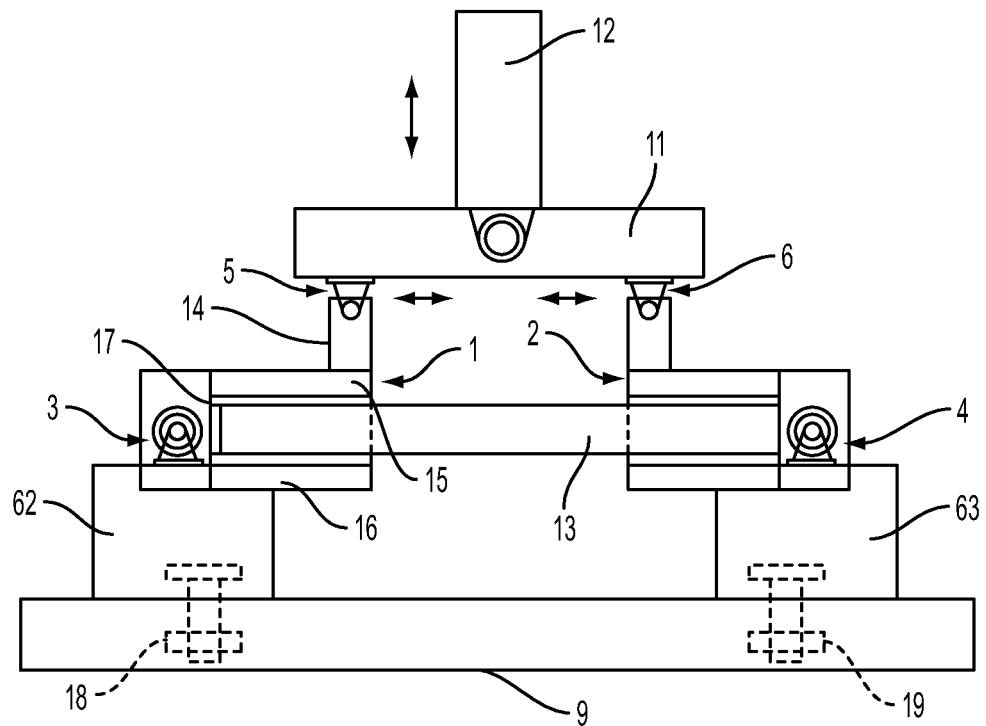
FIG. 6A is an elevation view of yet another exemplary apparatus for testing reversal bending fatigue in a horizontally oriented beam.
Figure 6B:
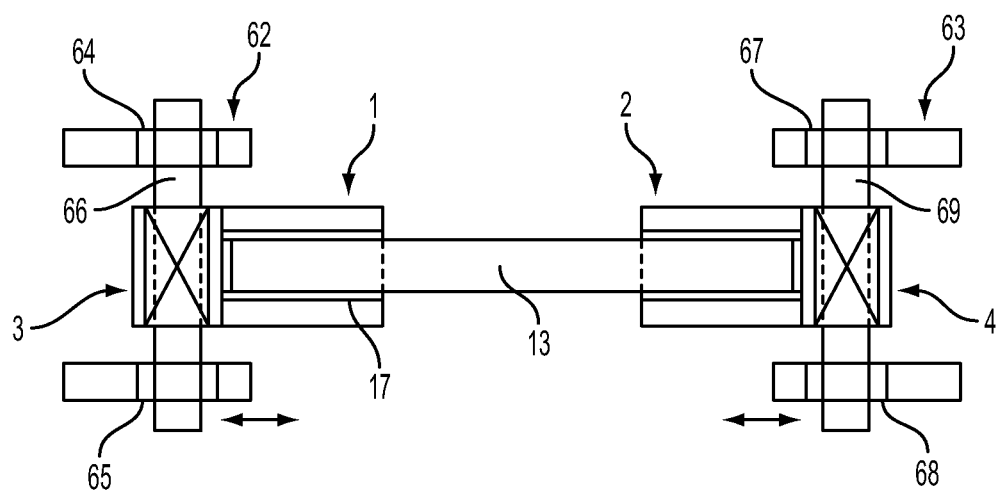
FIG. 6B is a plan view of the apparatus of FIG. 6A, with an upper portion removed for added clarity.

FIGS. 6A and 6B illustrate another embodiment of a fixture for bending fatigue testing. In this embodiment, the lower connections 3, 4 comprise a pivoting and sliding interface between the sleeves 1, 2 and two horizontal cross-shafts 66, 69, respectively. As shown in FIG. 6B, the connections 3, 4 allow the sleeves 1, 2 to translate laterally along the longitudinal axis of the cross-shafts 66, 69 (up and down in FIG. 6B). To accomplish this, precision bearings can be used between the sleeves and the cross-shafts. The cross-shafts 66, 69 can be cylindrical and the sleeves can comprise correspondingly sized horizontal openings mounted around the cross-shafts. The cross-shaft 66 can be supported at either end by a pair of base plates 62 and the cross-shaft 69 can be supported at either end by a pair of base plates 63. The cross-shafts 66, 69 can be coupled to the base plates 62, 63 via slide connections 64, 65 and 67, 68. The slide connections 64, 65 can permit the cross-shaft 66 to translate in the longitudinal direction of the beam 13 (left and right in FIG. 6B) relative to the base plates 62, while restricting the cross-shaft 66 from moving vertically or axially. Similarly, the slide connections 67, 68 can permit the cross-shaft 69 to translate in the longitudinal direction of the beam 13 (left and right in FIG. 6B) relative to the base plates 63, while restricting the cross-shaft 69 from moving vertically or axially. The base plates 62 and 63 can be fixed relative to the floor 9 via bolts 18 and 19.

In the embodiment of FIGS. 6A and 6B, the sleeves 1, 2 and the beam 13 are enabled to translate side-to-side via the precision bearings of connections 3, 4 through the parallel translation of the sleeves 1, 2 along the cross-shafts 66, 69. At the same time, the sleeves 1, 2 and the cross-shafts 66, 69 are permitted to slide together in the longitudinal direction of the beam 13 via the slide-connections 64, 65, 67, 68. Thus, in this embodiment, both horizontal and vertical shear stresses, as well as axial stress, can be released from the intermediate portion of the beam 13 such that a pure bending condition can exist in the intermediate portion of the beam. At the same time, the cross-shafts 66, 69 can serve a base on which the sleeves 1, 2 can rest when they are unloaded.

Prior to testing a beam, a standard specimen can be loaded to calibrate and align support plates 62, 63 and their corresponding slide connections 64, 65, 67, 68 and cross-shafts 66, 69 with the top loading beam 11. Reversed bending of the beam 13 results from oscillatory movement of loading rod 12. During a downward deflection of the beam 13, the upper connections 5, 6 slide towards each other due to the clockwise and counter-clockwise rotations of the left and right sleeves 1, 2, respectively. The downward deflection also creates a synchronized translation of the two cross-shafts 66, 69 on the support plates 62, 63 in the longitudinal direction of the beam. The cross-shafts move away from each other during downward deflection of the beam, releasing any axial force that would otherwise be imparted on the beam. The opposite rotations of sleeves 1, 2 occur in an upwards deflection of the beam 13, corresponding to the separation of upper connections 5, 6 and the convergence of cross-shafts 66, 69 via slide connections 64 and 65, 67 and 68, respectively.

Exemplary Vertical Embodiments

Figure 7:
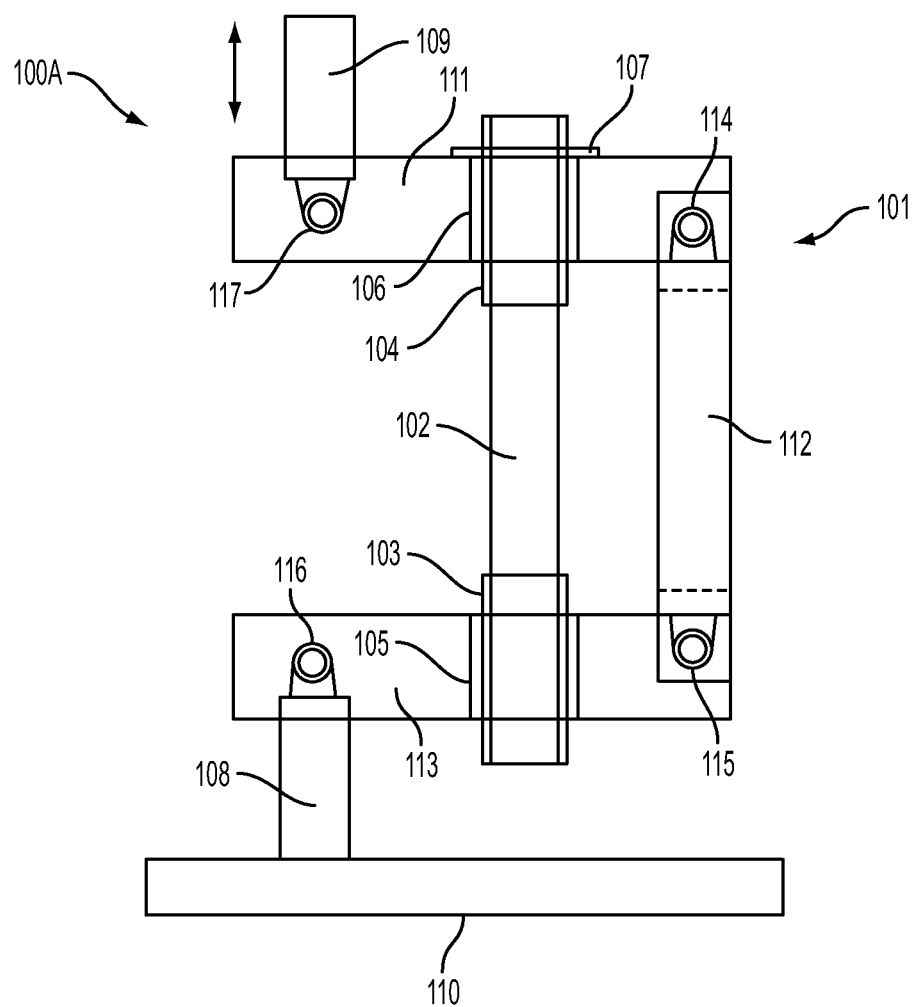
FIG. 7 is an elevation view of an exemplary apparatus for testing reversal bending fatigue in a vertically oriented beam.

FIG. 7 illustrates another embodiment of a bending fatigue testing apparatus 100A wherein the beam 102 is oriented vertically. This embodiment comprises a U-frame structure 101 that comprises two horizontal rigid arms 111, 113 and a vertical member 112 that is pivoted at either end with the two arms 111, 113 via pivot connections 114, 115, respectively. The vertical member 112 is also referred to herein as a linkage that links the two arms 111 and 113. The arms 111, 113 of the U-frame setup 101 can be linked to a host testing machine via a lower support rod 108 and an upper loading rod 109 through respective pivot connections 116, 117. The beam 102 is coupled to the rigid arms 111, 113 through respective roller bearings 105, 106 or equivalent bearing sets. The end portions of the beam 102 can be encapsulated with rigid sleeves 103, 104.

Figure 8:
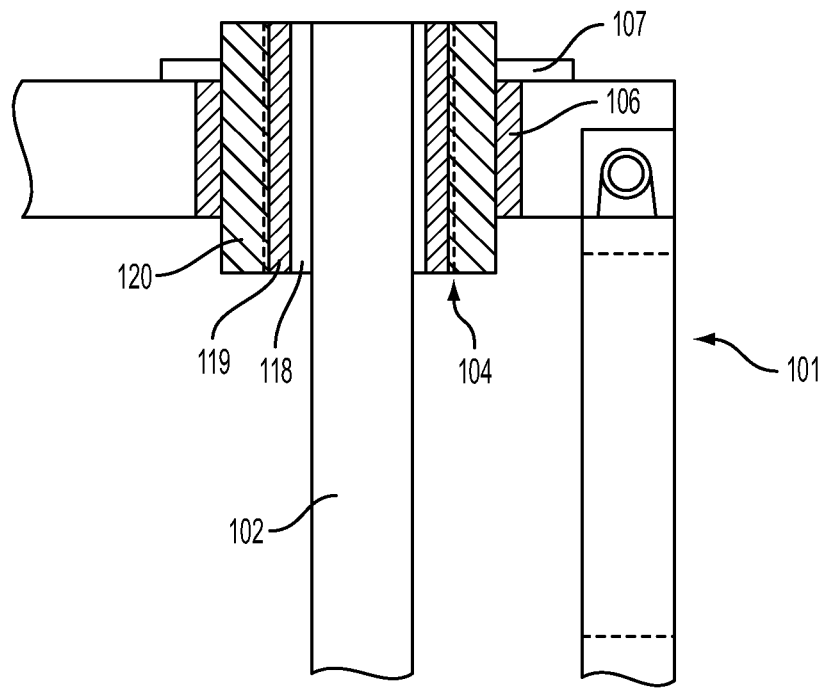
FIGS. 8 and 9 are cross-sectional views of an exemplary interface between a test beam and the apparatus of FIG. 7.
Figure 9:
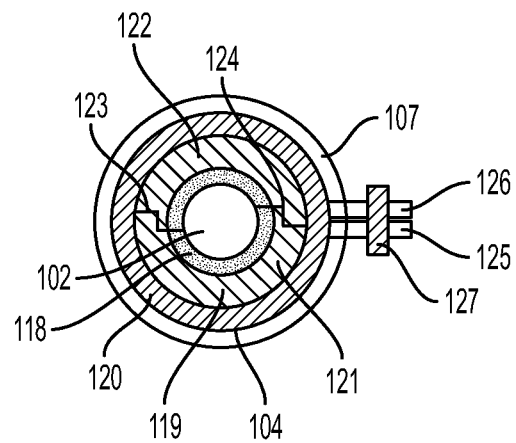

As shown in FIGS. 8 and 9, each of the rigid sleeves 103, 104 can be comprised of double sleeve layers with a split threaded inner sleeve 119 and an outer sleeve 120 positioned around the inner sleeve. The inner sleeve 119 can comprise two halves 121, 122 that can be clamped around the beam 102. The contact surfaces of inner and outer sleeves 119, 120 can be threaded with matching dimensions such that the outer sleeve 120 can be threaded over the inner sleeve 119 to secure the two halves 121, 122 onto the beam 102. A compliant layer 118, such as a polymeric material, can be sandwiched between the beam 102 and the inner sleeve 119.

As shown in FIG. 9, an encapsulation process can generally involve lining the inner sleeves 119 with the compliant layer 118 first, attaching the split inner sleeve halves 121, 122 with the matching interfaces 123, 124, and threading the outer sleeve 120 onto the inner sleeve. The preload can be applied to close the gap on the interfaces 123, 124 between the two halves by using a clamping tool (not shown). The degree of preloading can be controlled to ensure contact between the specimen and the inner sleeve. The encapsulated beam 102 can be equipped with an upper collar, or flange, 107 fixed to the outer sleeve 120 that serves as a stop when the beam 102 is inserted into the paired bearings 105, 106. The collar 107 can have a width dimension that is greater than the width of the bearing opening 106 such that the collar 107 is stopped from falling downward through the opening, but does not otherwise restrict the longitudinal movement of the beam 102. As shown in FIG. 9, the collar 107 can comprise an annular member positioned around the outer sleeve 120, a pair of handles 125, 126 that extend radially, and a set screw 127 for fixing the handles 125, 126 together to clamp the collar 107 onto the outer sleeve.

Figure 10:
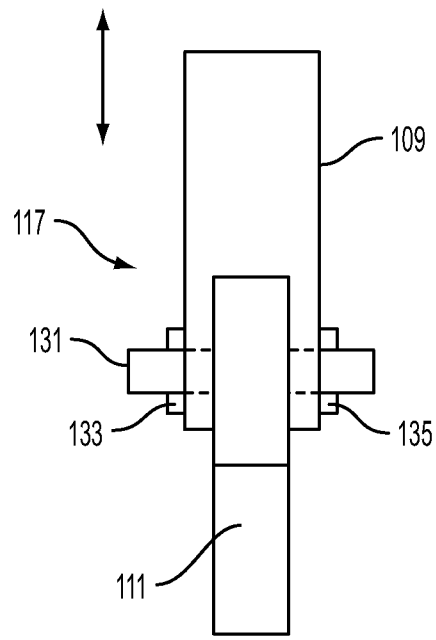
FIGS. 10 and 11 show exemplary upper and lower pivot connections of the apparatus of FIG. 7.
Figure 11:
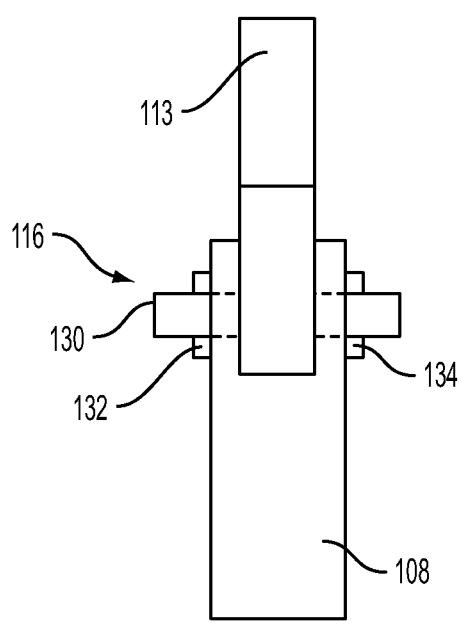

As shown in FIG. 10, the pivot connection 117 can comprise a roller 131 to transfer the loading between the loading rod 109 and the arm 111. Two pins 133, 135 can be used to secure the roller 131 in position during cyclic (e.g., vibrational) loading. As shown in FIG. 11, the pivot connection 116 between the lower arm 113 and the support 108 can be constructed similarly. A roller 130 can be used to transfer the loading between the support rod 108 and the arm 113. Two pins 132, 134 can be used to secure the roller 130 in position during cyclic loading.

Figure 12:
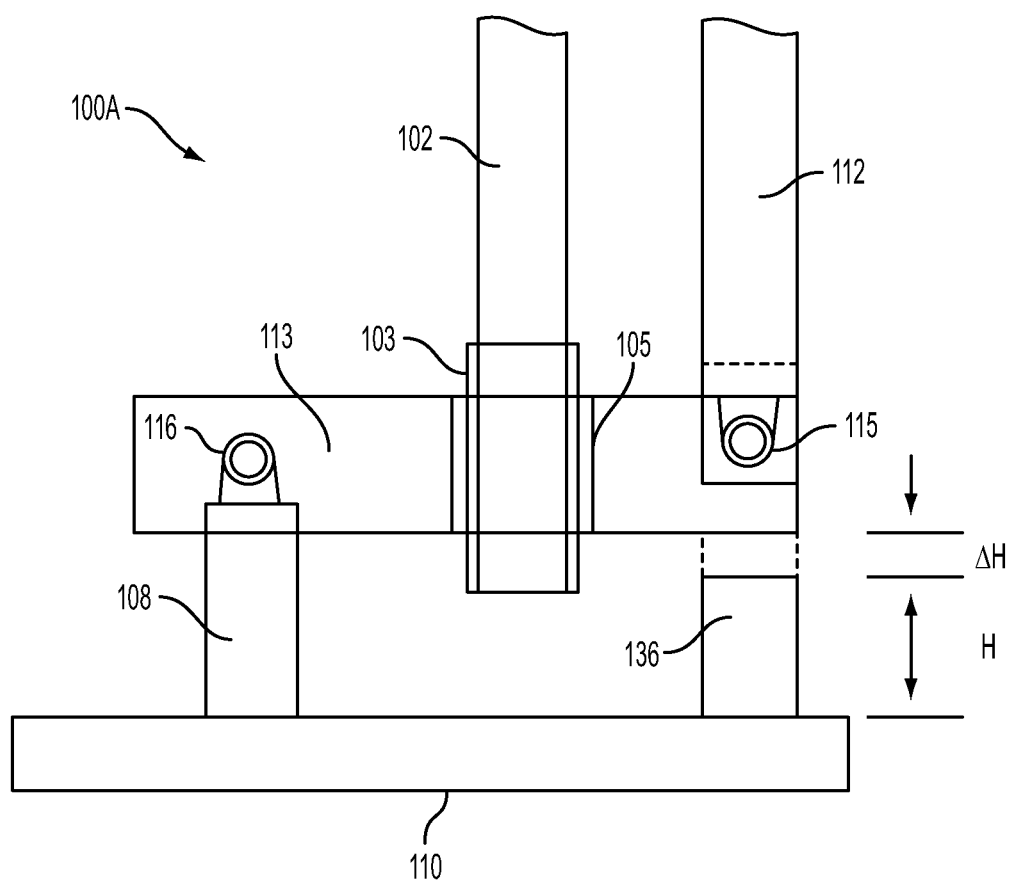
FIG. 12 shows an exemplary temporary support mechanism for the apparatus of FIG. 7.

The arms 111, 113 and vertical member 112 of U-frame 101 can be rotatable relative to one another due to the pivot connections 114, 115, creating a non-rigid structure. Accordingly, as shown in FIG. 12, a support 136 can be placed underneath the vertical member 112 of the U-frame 101 to assist its setup for beam loading. An actuation mechanism can selectively adjust the height of the support 136 by ΔH so as to reach out and support the U-frame 101 during setup to keep the U-frame in a desired shape (e.g., the connections 114, 115 at right angles). After a beam 102 is loaded into the U-frame, the support 136 can be retracted.

A standard specimen can be used to calibrate the position of the support 136 on the floor of the host machine and to align the U-frame 101 with the loading plane prior to the initial setup of the testing beam. The testing beam 102 can be prepared first with its two ends encapsulated (FIG. 8), and then can be inserted into the co-axial holes of the arms 111, 113. The insertion of the beam 102 can be stopped when the stopping collar 107 hits the top of the upper arm 111. The U-frame 101 can transform into a semi-rigid structure once it is loaded with the beam 102. Afterwards, the temporal support device 136 can be withdrawn.

For the embodiment shown in FIGS. 7-12, reversal bending on the tested beam 102 can be performed by opening and closing the two arms 111, 113 (i.e., moving the pivot connections 116 and 117 toward and away from each other) at a desired frequency. The extent of rotation of the arms 111, 113 about the pivot connections 114, 115 depends on the forces applied to the arms as introduced by the host actuation system through the support and loading rods 108, 109. The roller bearings 105, 106 can be designed to release the axial force related to the flexure of the beam 102 and, at the same time, enable the formation of the bending moments through variable normal pressure on opposite bearing surfaces. Through the roller bearings 105, 106, the generated bending moments are transferred into the beam 102, while the introduced vertical load is directed to the vertical member 112 through the upper arm 111 and then down to the base 110 via the lower arm 113 and the lower support member 108. A closing force on the arms produces counter-clockwise and clockwise force couples at the upper and lower ends of the testing beam 102, respectively. This results in a deflection of the testing beam 102 in the right direction. Conversely, an opening force on the arms generates clockwise and counter-clockwise force couples at the upper and lower end portions of the beam, resulting in a deflection in the left direction.

The external bending load is fully exerted on the beam 102 in this embodiment due to the pivot connections 114, 115 at the top and bottom of the vertical member 112. If the net vertical loading force is P, the net bending moment to the beam is MI, the length of U-frame arms 111, 113 (from the pivot connections 114, 115 to the pivot connections 116, 117) is L, then we have the following equation:

$$M1 = P*L. \tag{1B}$$

The equation 1B does not consider the effect of buckling on the bending in the axially-loaded vertical member 112 as it can be designed to be sufficient strong.

Figure 13:
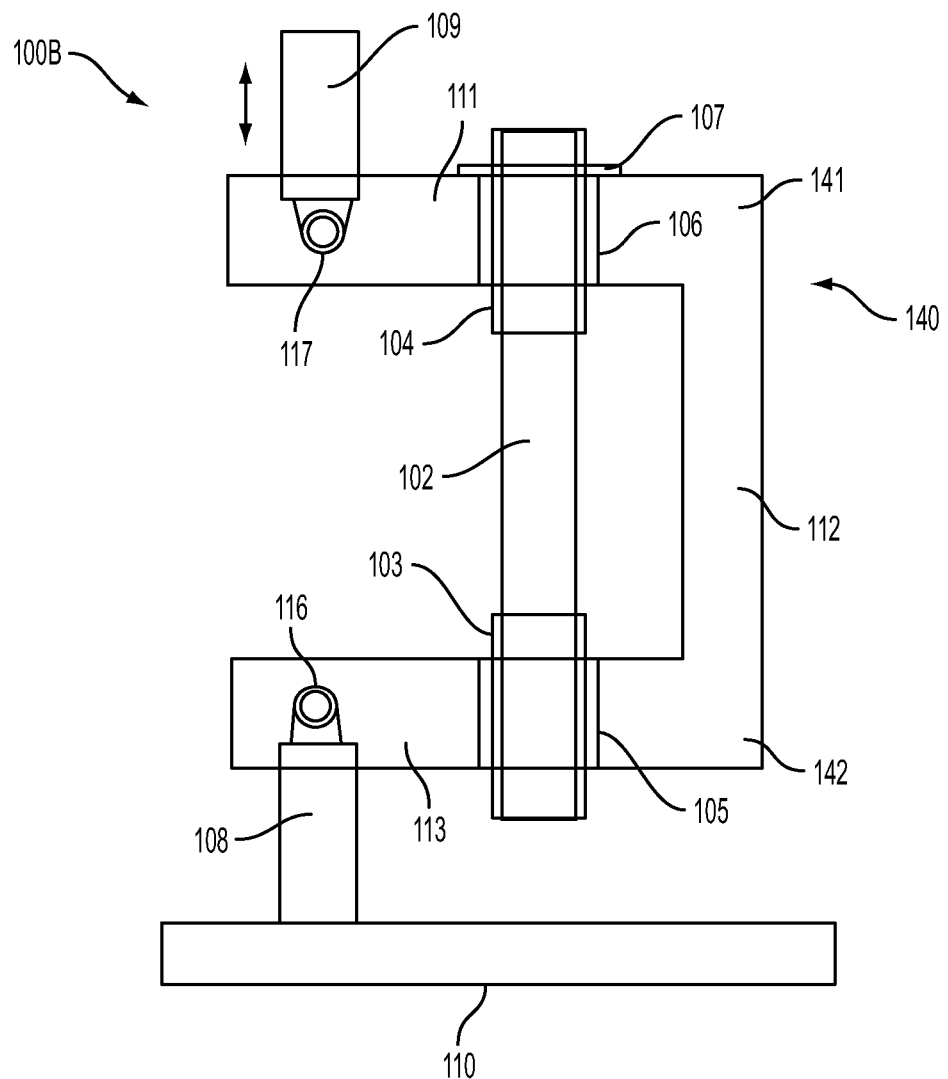
FIG. 13 is an elevation view of another exemplary apparatus for testing reversal bending fatigue in a vertically oriented beam.
Figure 13A:
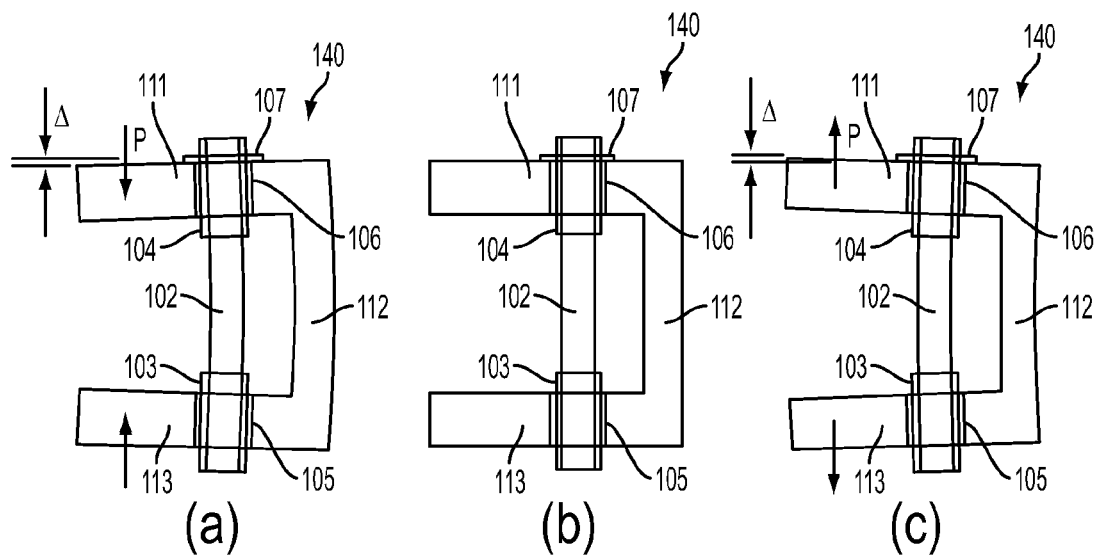
FIGS. 13A and 13B show exemplary forces and moments applied to the apparatus of FIG. 13, and associated deformation.
Figure 13B:
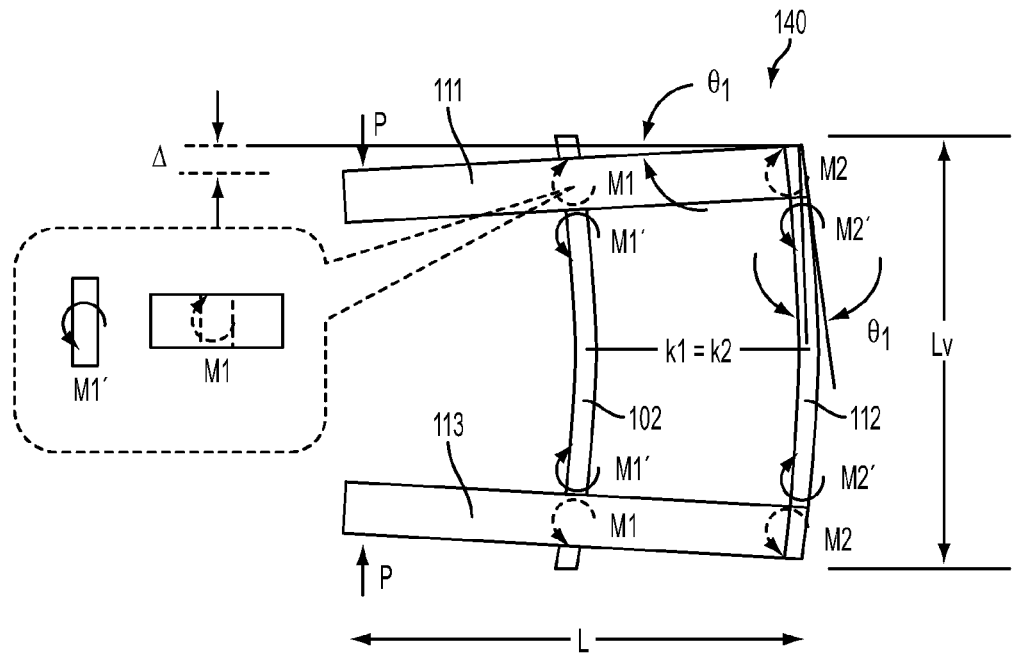
Figure 14:
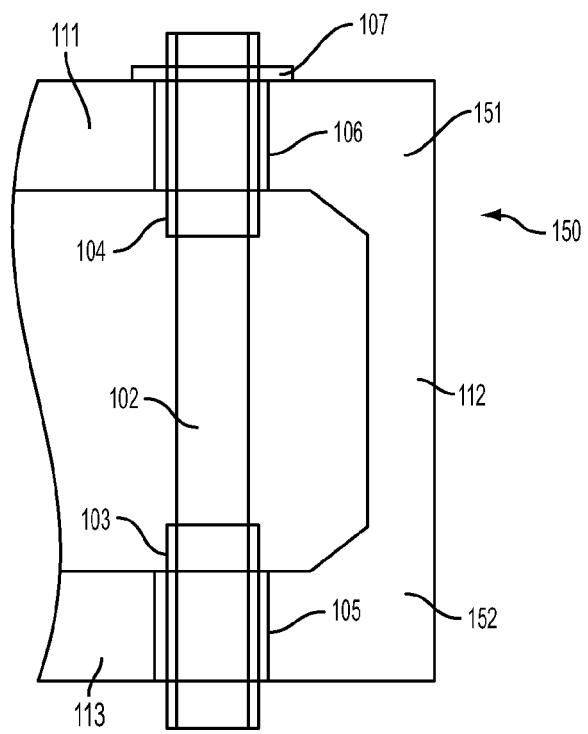
FIG. 14 shows an alternative embodiment of the apparatus of FIG. 13, with reinforced corners.
Figure 15:
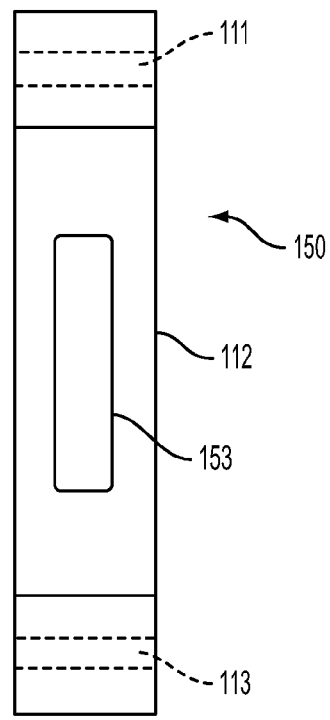
FIG. 15 shows an exemplary vertical member of the apparatus of FIG. 13.

FIG. 13 illustrates another embodiment 100B with the beam 102 oriented vertically where the U-frame 140 is constructed with two rigid arms 111, 113 and a vertical member 112 that are joined rigidly with two rigid corners 141, 142. FIGS. 13A and 13B illustrate corresponding reversal bending motions and forces. As illustrated in FIGS. 14 and 15, the web thickness of the vertical member 112 can be reduced to make the vertical member appropriately flexible for the corresponding beam 102 and loading pattern. In one example shown in FIG. 15, the vertical member 112 can comprise an opening 153 in the web to produce the required flexibility by altering/reducing the cross-sectional area.

Prior to inserting a beam 102 for testing, the position of lower support 108 can be calibrated against the loading rod 109 using a standard specimen. The testing beam 102 can then be prepared with the ends encapsulated with the rigid sleeves 103, 104. Because the rigid corners 141, 142 can enable the U-frame 140 to stand rigidly by itself, the routine setup of the testing specimen can involve merely the insertion of the beam 102 into the coaxial holes of the arms 111, 113. In some embodiments, the stop collar 107 is used to prevent the beam 102 from falling in the vertical direction.

Figure 16:
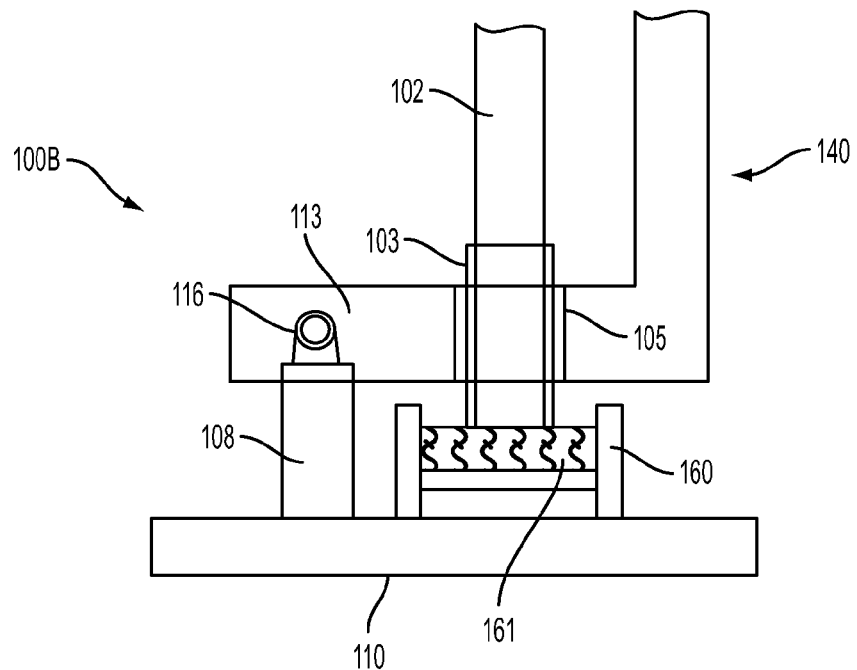
FIG. 16 shows an exemplary support mechanism for the apparatus of FIG. 13.

In another embodiment shown in FIG. 16, a compliant and/or resiliently deformable material 161 can be used to support the lower end of the beam 102 during testing. The material 161 can be supported on the floor 110 via supports 160.

Reverse bending of the beam 102 can be accomplished by opening and closing the two rigid arms 111, 113 of the U-frame 140, as shown in FIG. 13A. In a typical testing process, for example, in closing the rigid arms, the two arms 111, 113 can approach each other due to the compressive force from the loading rod 109 and reactive force from support 108. The closing of the arms 111, 113 imposes bending moments on the vertical member 112 and forces it to deflect toward the right. The bending moment is shared by the beam 102 due to its precise coupling with the bearings 105, 106 of the rotating arms 111, 113. On the upper bearing 106, two opposite variable pressure distributions act on the two half-cylindrical surfaces of rigid sleeve 104 and their resultants create a counter-clockwise bending moment on the upper end of the beam 102.

Meanwhile, the lower bearing 105 imposes a bending moment of equal magnitude but in clockwise direction on the lower rigid sleeve 103. Therefore, a symmetrical bending is concurrently generated in intermediate portion of the beam 102 with the deflection direction the same as in the vertical member 112. The partition of the bending moment between the beam 102 and the vertical member 112 depends on the relative bending moduli of each component.

The opening/separation of rigid arms 111, 113 similarly creates a defection of beam 102 and vertical member 112 toward the left.

Because the roller bearings 105, 106 are designed to transfer only the normal pressure but not the axial force, the vertical load from upper loading rod 109 is directed to the vertical member 112 through the upper arm 111 and then to the support 108 through the lower arm 113. The vertical member 112 can act as a two-dimension beam subject to both bending moment and axial force and can be configured to work stably without buckling.

The bending moment applied to the tested beam 102 is related to the concentrated force, the length of U-frame arms 111, 113, and bending moduli of vertical member 112. Let the concentrated vertical force be P, the bending moment to the beam be M1, the length of arms be L, the bending modulus of the beam be $(EI)_1$ and the bending modulus of the vertical member 112 be $(EI)_2$. Considering the effect of axial loading on bending moment is negligible as the deformation is sufficiently small, then we have the following equation (from curvature point, both the test beam and vertical arm have the same curvatures):

$$M1 = (EI)_1 / [(EI)_1 + (EI)_2] * P * L \quad (2)$$

This illustrates how the total bending moment P*L is partitioned between the beam specimen 102 and vertical member 112. With reference to FIG. 13B, the bending moment on the beam specimen M1 can also be estimated according to the displacement Δ of the rigid arm 111 and the length $L_v$ of the vertical member 112 as follows:

$$M1 = P*L - [2*(EI)_2*/L_v]*(\Delta/L) \quad (3)$$

Figure 17:
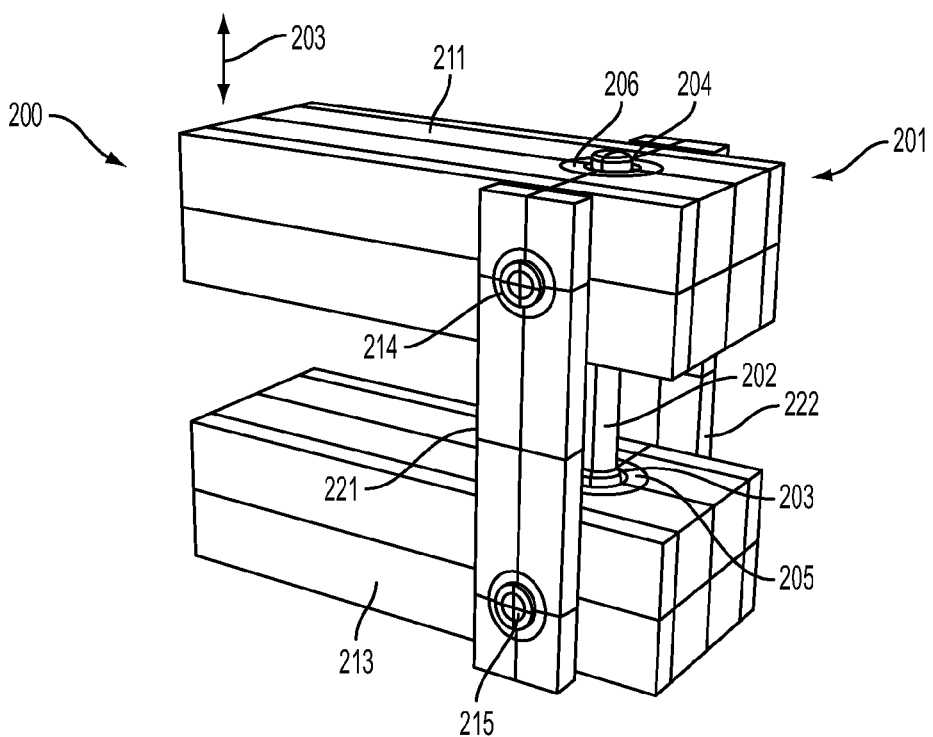
FIG. 17 is a perspective view of yet another exemplary apparatus for testing reversal bending fatigue in a vertically oriented beam.

FIG. 17 illustrates another embodiment 200 with the beam 202 oriented vertically where the vertical member 112 is replaced by two parallel vertical connecting plates 221, 222 positioned on either side of the beam 202. The plates 221, 222 are pivotally coupled to the upper arm 211 and lower arm 213 through respective pivot pins 214 and 215. The plates 221, 222 are also referred to herein collectively as a linkage that links the arms 211, 213. The plates 221, 222 are also shifted from the ends of rigid arms 211, 213 to a position such that they are co-planar with the beam 202 (i.e., a vertical plane defined by the pivot axes 213, 214 and the longitudinal axis of the beam 202). Compliance sleeves can be positioned at the interfaces between the end portions of the beam 202 and the arms 211, 213. In addition, the interfaces can comprise rigid sleeves 203, 204 and associated respective roller bearings 205, 206.

With the enforced mechanical load 203, the embodiment 200 can have a constant (fixed) gage length. Because all of the bending moment is delivered to the beam 202, it can be capable of delivering more power to the beam 202 under cyclic fatigue testing. The enforced bending moment can be estimated according to Eq. 1B.

Figure 18:
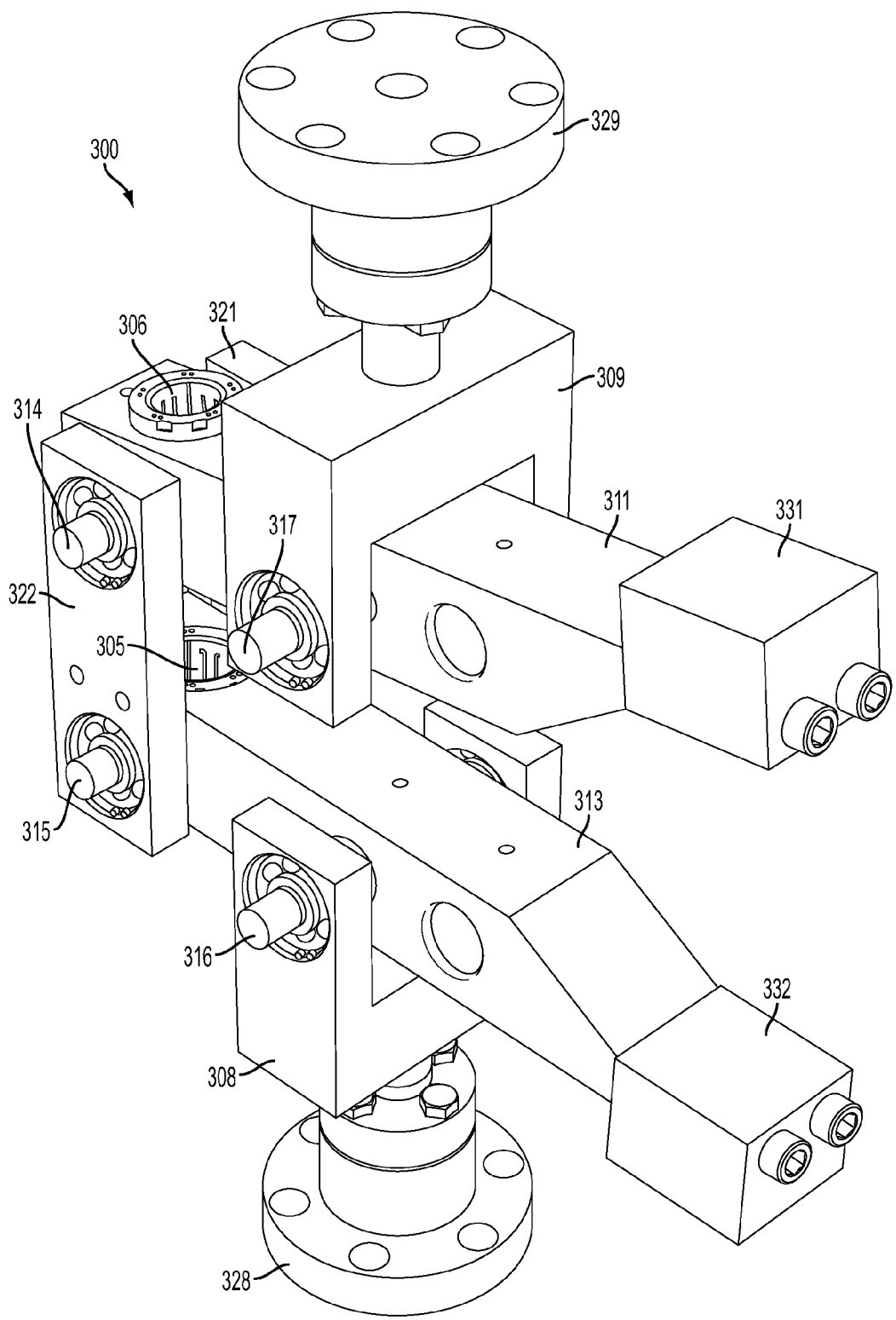
FIG. 18 is a perspective view of yet another exemplary apparatus for testing reversal bending fatigue in a vertically oriented beam, including counterweights.

FIG. 18 illustrates another embodiment 300 for testing a beam oriented vertically. This embodiment is similar to the embodiment 200 of FIG. 17 in that it comprises an upper rigid arm 311, a lower rigid arm 313, and a pair of vertical plates 321, 322 positioned on either side of the arms adjacent to location of the test beam (the beam is not shown in FIG. 18) and pivotally coupled to the upper arm 311 via a pivot connection 314 and pivotally coupled to the lower arm 313 via a pivot connection 315. The plates 321, 322 are also referred to herein collectively as a Linkage that links the arms 311, 313.

The embodiment of FIG. 18 further comprises a forked upper loading member 309 pivotally coupled to the upper arm 311 via a pivot connection 317, and a forked lower loading member 308 pivotally coupled to the lower arm 313 via a pivot connection 316. Each of the pivot connections 314, 315, 316, 317 can be substantially parallel to one another and can comprise high precision bearings to minimize backlash. An upper adapter 329 can be coupled to the upper loading member 309 and a lower adapter 328 can be coupled to the lower loading member 308 to facilitate coupling the apparatus to a machine that can provide an oscillating load on the loading members to pivot the arms toward and away from each other at a desired frequency and magnitude.

The upper arm 311 can comprise an upper bearing set 306 for receiving the upper end portion of the test beam and the lower arm 313 can comprise a lower bearing set 305 for receiving the lower end portion of the test beam. Two specimen retainers (not shown) can be placed below the bearing set 305 and above the bearing set 306 to prevent the specimen from falling or sliding out. Springs or similar elastically resilient materials can be used between the retainers and the specimen ends to provide a desired freedom of axial motion. As shown in FIG. 18, counterweights 331, 332 can be coupled to the ends of the arms 311, 313, respectively. The counterweights can help balance the weight of the apparatus 300 about the pivot connections 316, 317 in order to eliminate undesirable gravitational forces introduced due to the vertical setup. The counterweights 331, 332 can be removable and/or adjustable in weight and position in order to tune the apparatus for specific loading conditions.

Embodiments wherein the test beam is oriented vertically can have advantages compared to embodiments wherein the beam is oriented horizontally. With vertical embodiments, bending moments can be applied through two horizontal rigid arms of a U-frame structure and the arms can be equipped with two co-axial holes that accommodate the beam to be tested. The roller bearings or equivalent bearing sets in the arms of U-frame can allow the release of any axial load related to the loading of the beam and, at the same time, can transfer the bending moments from the rigid arms to the beam. The U-frame of the vertical embodiments can have fewer components, which can result in a test system with enhanced reliability and controllability. The setup of a test beam in the vertical embodiments can be accomplished by a simple insertion of the beam into the holes in the arms, which can be advantageous for a hot-cell environment because most hot-cell operations can be adapted for the vertical testing systems.

Additional Embodiments

Figure 19:
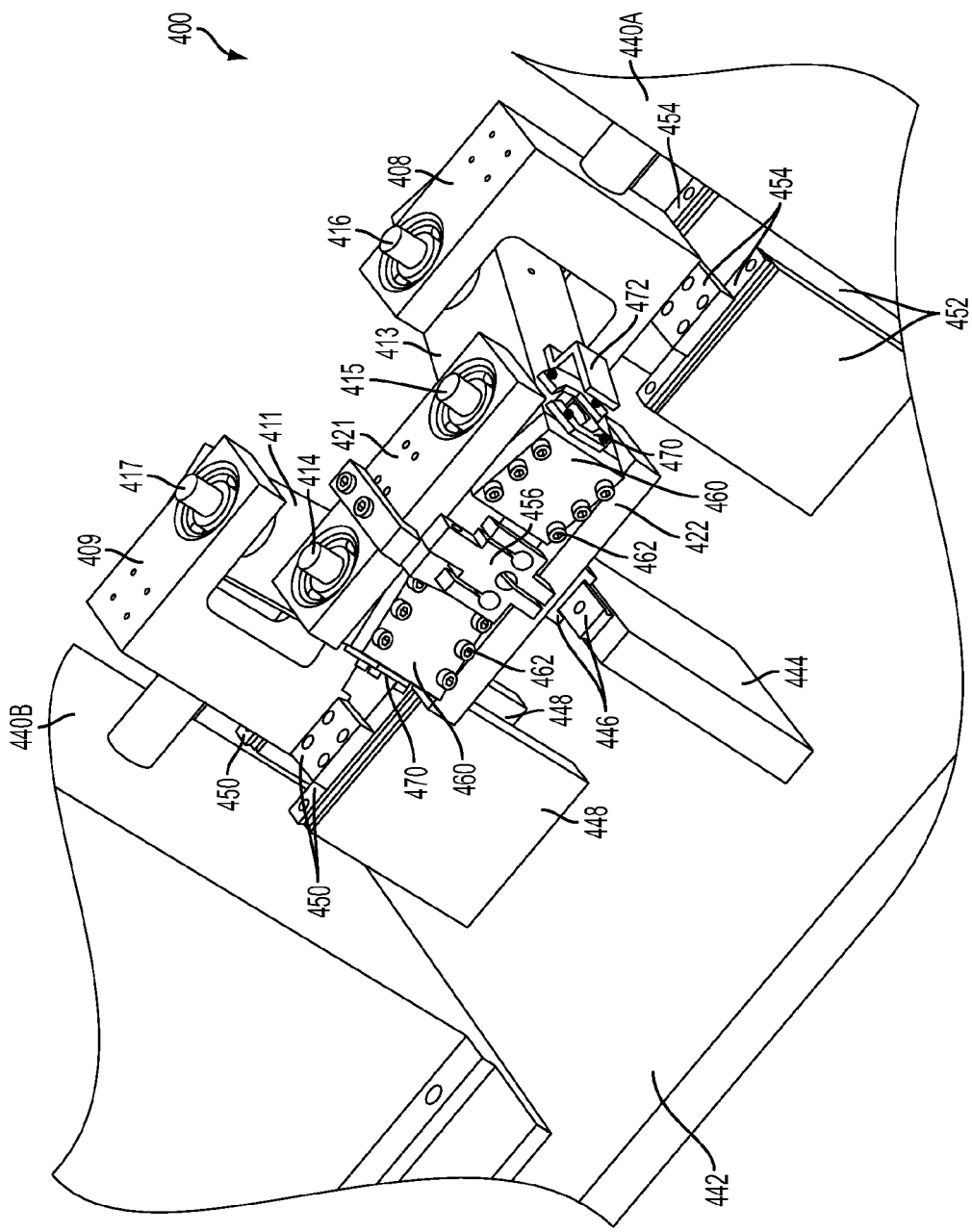
FIG. 19 is a perspective view of an exemplary system for testing reversal bending fatigue in a horizontally oriented beam.

FIG. 19 illustrates another embodiment 400 for testing reversal bending fatigue in a test beam (not shown in FIG. 19) with the test beam oriented horizontally. Though the beam is oriented horizontally, this embodiment is similar to the vertical embodiment 300 of FIG. 18, with the apparatus rotated 90° and without the counterweights 331, 332. In embodiment 400, a test beam is tested with its longitudinal axis extending horizontally, and is caused to bend in a horizontal plane. This is different than the embodiments of FIGS. 1-6, wherein the beam is oriented horizontally, but the beam is caused to bend up and down in a vertical plane.

The embodiment of FIG. 19 comprises a first rigid arm 411, a second rigid arm 413, and a pair of horizontal plates 421, 422 positioned on upper and lower sides, respectively, of the arms 411, 413 adjacent to location of the test beam (the beam is not shown in FIG. 19) and pivotally coupled to the first arm 411 via a vertical pivot connection 414 and pivotally coupled to the second arm 413 via a vertical pivot connection 415. The horizontal plates 421, 422 are also referred herein collectively as a linkage that links arms 411, 413. The embodiment 400 further comprises a first forked loading member 409 pivotally coupled to the first arm 411 via a vertical pivot connection 417, and a second forked loading member 408 pivotally coupled to the second arm 413 via a vertical pivot connection 416. Each of the vertical pivot connections 414, 415, 416, 417 can be substantially parallel to one another and can comprise high precision bearings to minimize backlash. The loading members 408, 409 can be coupled to a testing device 440 that can provide an oscillating load horizontal on the loading members 408, 409, such as via linear motors, to pivot the arms 411, 413 toward and away from each other at a desired frequency and magnitude.

The testing device 440 can comprise two laterally spaced apart actuation components 440A, 440B that are coupled to the loading members 408, 409, respectively, and are fixed relative to each other via a rigid floor 442. The actuation components 440A, 440B can be mounted in an adjustable manner to the floor 442 such that the horizontal distance between them can be adjusted. The lower plate 422 can be vertically supported by a central support 444 that is fixed to the floor 442. A slide connection 446 can couple the vertical support 444 to the lower plate 422 to allow the lower plate 422 to freely translate in a horizontal plane while restricting any vertical motion. Similarly, the first loading member 409 can be vertically supported by a vertical support 448 that is fixed to the floor 442. A slide connection 450 can couple the vertical support 448 to the first loading member 409 to allow the loading member 409 to freely translate in a horizontal plane while restricting any vertical motion.

The second loading member 408 can be vertically supported by a vertical support 452 that is fixed to the floor 442. A slide connection 454 can couple the vertical support 452 to the second loading member 408 to allow the loading member 408 to freely translate in a horizontal plane while restricting any vertical motion. The slide connections 446, 450, 454 can comprise high precision bearings to reduce backlash.

Figure 20:
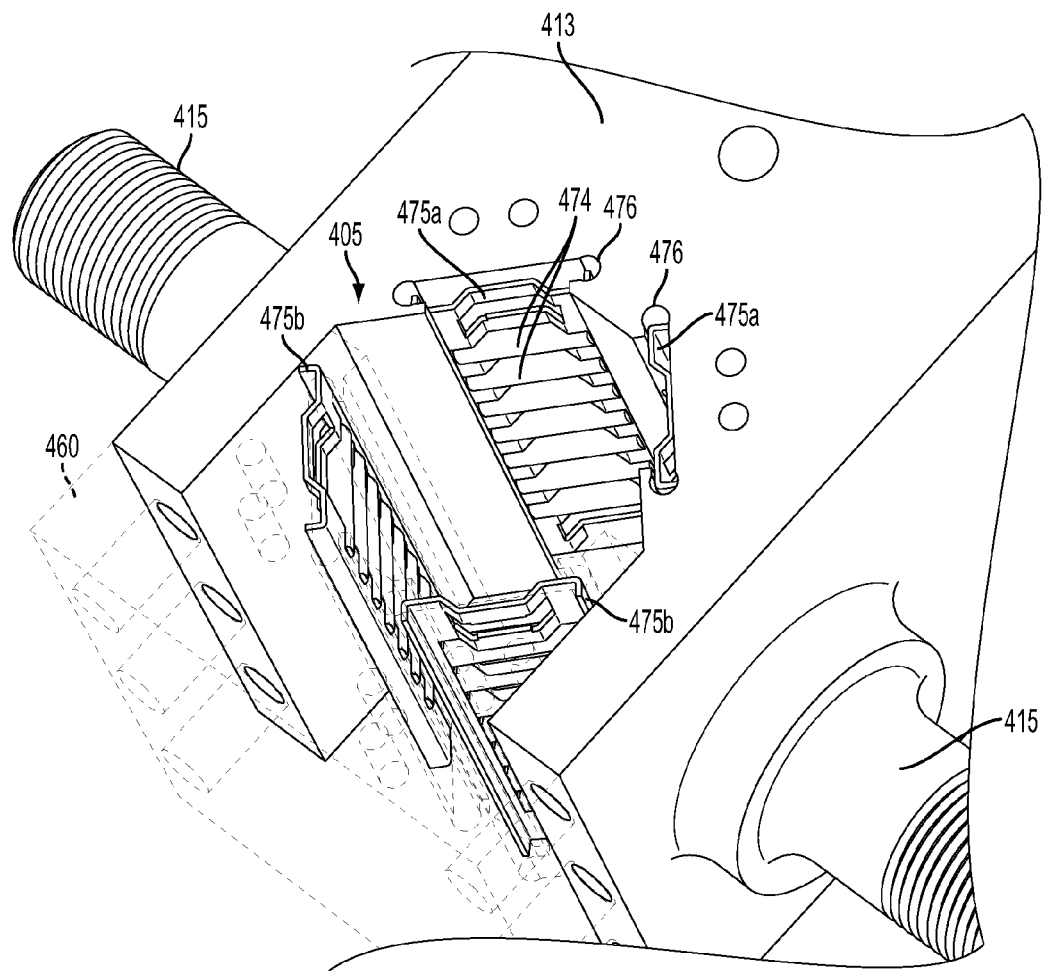
FIG. 20 is a perspective view of an end of one arm of the apparatus of FIG. 19, with an adjustable end piece shown in dashed lines.
Figure 21:
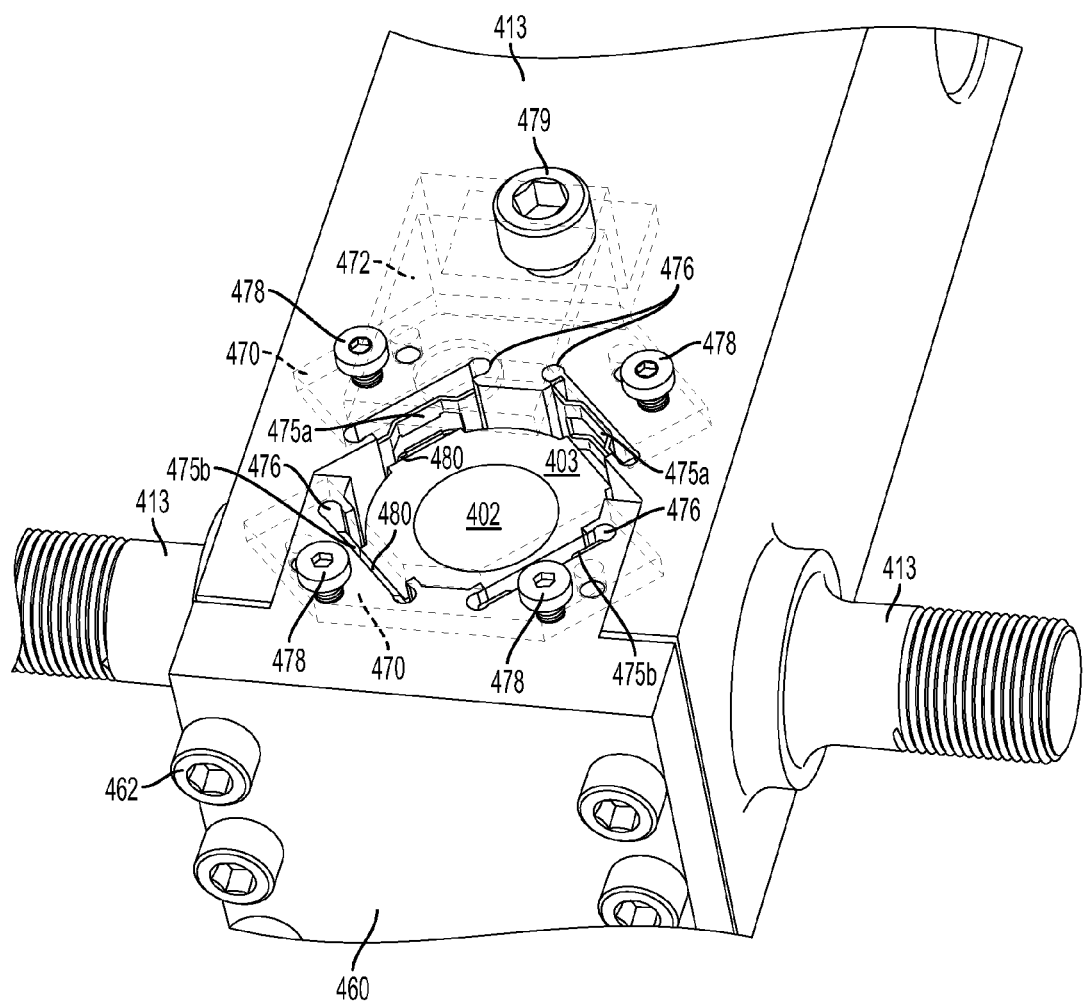
FIG. 21 shows the arm of FIG. 20 with various retaining components shown in dashed lines.

As illustrated in FIGS. 20 and 21, the first arm 411 can comprise a first bearing set 406 for receiving one end portion of the test beam and the second arm 413 can comprise a second bearing set 405 for receiving the other end portion of the test beam. As shown in detail in FIG. 20, each of the bearing sets 405, 406 can comprise a plurality of rollers 474 mounted in brackets 475. Each bracket 475 can support a plurality of rollers 474 such that the rollers 474 can rotate about parallel axes. Each bearing set 405, 406 can comprise a plurality of brackets 475, each supporting plural rollers 474, disposed around the circumference of an opening for receiving one end portion of a test beam. The illustrated embodiment comprises four brackets 475 disposed at 90° increments around the circumference of the opening. The brackets 475 can be coupled to the arm 413 in a fixed manner and aligned such that the rollers 474 are configured to allow a test beam inserted into the opening to freely move in its axial direction.

Each of the arms 411, 413 can comprise a removable and/or adjustable end piece 460, as shown in FIGS. 20 and 21. The end piece 460 can be coupled to the main portion of the arm via fasteners 462, such as screws. In the illustrated embodiment, two of the brackets 475a are mounted in recesses 476 in the arm 413, while the other two brackets 475b are mounted to end piece 460. With the end piece 460 removed or loosened relative to the arm 413, the opening for receiving the beam can be widened, with the brackets 475b spaced further apart from the brackets 475a. In this "open" configuration, the test beam can be inserted or removed from the apparatus.

As shown in FIG. 21, when the beam 402 is inserted for testing, the end pieces 460 can be tightened onto the arms 411, 413 such that the brackets 475b move closer to the brackets 475a and engage a rigid sleeve 403 covering the end portion of the beam 402. The rigid sleeve 403 can comprise flat outer surfaces 480 adapted to roll along the rollers 474.

As shown in FIG. 21, the roller brackets 475 can be secured in the recesses 476 and prevented from sliding axially with end plates, or spring clips, 470 (shown in dashed lines in FIG. 21) positioned over the recesses 476 and secured to the arm 413 and end piece 460 with fasteners 478. The end plates 470 are also shown in FIG. 19. End stops 472 can be coupled to the arms 411, 413 to provide a limit to the axial translation of the test beam 402. Exemplary end stops 472 are shown in dashed lines in FIG. 21 and shown in solid lines in FIG. 19. The end stops 472 can be secured to the arms 411, 413 with a removable fastener 479. One of the end stops 472 can be removed in order to insert a test beam axially into the bearing sets 405, 406, then the end stop 472 can be repositioned to block the axial path of the test beam to prevent it from sliding out of the bearing sets. The end stops 472 can be configured to be spaced a desired distance from the ends of the beam 402 to allow for a desired amount of axially travel for the beam relative to the bearing sets. In some embodiments, springs or similar elastically resilient materials can be positioned between the ends of the beam 402 and the end stops 472 to provide a cushioned interface and/or dampen axial motion of the beam.

As shown in FIG. 19, a bracket 456 can be coupled to the plates 421, 422 to support one or more sensors (not shown). Sensors can comprise linear variable differential transformers (LVDTs), for example, for measuring linear displacement of the intermediate portion of the beam during testing. These sensors can be used to measure the magnitude and frequency of the deflection in the intermediate portion of the beam. The illustrated bracket 456 comprises three slots for supporting LVDTs at three different axial locations along the beam. Additional and/or alternative sensors can also be included for other purposes.

In operation, the horizontal embodiment of FIG. 19 can cause the test beam to deflect in a horizontal plane substantially perpendicular to the vertical pivot axes 414, 415. Because the oscillatory motions are horizontal and the components are vertically supported by supports 444, 448, 452, the effects of gravity can be eliminated and no counterweights are needed for balance, allowing for a lighter, simpler configuration.

Currently, vibration has been included as a mandatory testing condition for the structural evaluation of a package in transporting SNF by US NRE (Nuclear Regulation Commission) in 10 CFR §71.71. Considering that a growing market exists in the processing and safe transportation of SNF and no testing system is available for the analysis of vibration integrity, the disclosed embodiments are anticipated to have a great application in this field in the near future. The disclosed embodiments and concepts can also be applied to other structural materials in general which need to have their fatigue strengths evaluated.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims. The disclosed apparatuses are available for licensing in specific fields of use by the assignee of record.

We claim:

1. An apparatus for testing reversal bending fatigue in an elongated beam, the beam having opposing first and second end portions and an intermediate portion between the first and second end portions, the beam having a longitudinal axis extending between the first and second end portions, the apparatus comprising:
   a first rigid arm having a load end portion, a linkage end portion, and a first opening for receiving the first end portion of the beam;
   a second rigid arm comprising a load end portion, a linkage end portion, and a second opening for receiving the second end portion of the beam;
   a linkage having a first end portion coupled to the linkage end portion of the first rigid arm and a second end portion coupled to the linkage end portion of the second rigid arm;
   a first bearing positioned within the first opening for allowing the beam to translate in the longitudinal direction of the beam relative to the first rigid arm;
   a second bearing positioned within the second opening for allowing the beam to translate in the longitudinal direction of the beam relative to the second rigid arm, the first and second bearings restricting translation of the beam perpendicular to the longitudinal direction of the beam when the beam is installed; and
   wherein pivoting the load ends portions of the first and second rigid arms in opposite directions causes the first bearing to exert a first bending moment on the first end portion of the beam and causes the second bearing to exert a second bending moment on the second end portion of the beam, resulting in a pure bending condition in the intermediate portion of the beam; and
   wherein cyclically alternating the direction of the first and second bending moments cause the intermediate portion of the beam to cyclically bend back and forth in opposite directions while remaining in a pure bending condition.

2. The apparatus of claim 1, wherein the linkage is coupled to the linkage end portion of the first rigid arm at a first pivot axis and is coupled to the linkage end portion of the second rigid arm at a second pivot axis, the first and second pivot axes being substantially parallel, the first rigid arm being pivotable relative to the linkage about the first pivot axis and the second rigid arm being pivotable relative to the linkage about the second pivot axis.

3. The apparatus of claim 1, wherein the linkage is fixed to the linkage end portions of the first and second rigid arms.

4. The apparatus of claim 1, wherein the apparatus further comprises a rigid annular sleeve positioned around the first end portion of the beam and an annular collar positioned around the sleeve and within the first bearing, the sleeve and collar being fixed relative to the beam, the collar having a flange portion configured to limit the translational motion of the beam relative to the first rigid arm in the longitudinal direction of the beam when the beam is installed in the apparatus.

5. The apparatus of claim 1, wherein the first bearing comprises a plurality of generally cylindrical rollers that are rotatable relative to the first rigid arm about respective axes generally perpendicular to the longitudinal axis of the beam.

6. The apparatus of claim 1, wherein the first rigid arm comprises an end piece that is adjustable in a direction perpendicular to the longitudinal direction of the beam and is configured to adjust the size of the first opening.

7. The apparatus of claim 1, wherein the apparatus is configured such that the longitudinal axis of the beam is generally horizontal and the beam deflects in a generally horizontal plane.

8. The apparatus of claim 1, wherein the apparatus is configured such that the longitudinal axis of the beam is generally vertical.

9. The apparatus of claim 8, further comprising a first counterweight coupled to the load end portion of the first rigid arm and a second counterweight coupled to the load end portion of the second rigid arm.

10. The apparatus of claim 1, wherein the linkage comprises first and second members positioned on opposite sides of the beam.

11. A method of testing reversal bending fatigue in an elongated beam, the method comprising:
   a) positioning a beam in a testing apparatus, the testing apparatus comprising a first rigid arm coupled to a first end portion of the beam and a second rigid arm coupled to a second end portion of the beam;
   b) applying a first bending moment to the beam to create a first pure bending condition in an intermediate portion of the beam, wherein applying the first bending moment to the beam includes applying opposing compressive forces on the first and second rigid arms, the compressive forces being generally parallel with a longitudinal axis of the beam; and
   c) applying a second bending moment to the beam, the second bending moment being substantially equal in magnitude and substantially opposite in direction relative to the first bending moment, to create a second pure bending condition in the intermediate portion of the beam, the second bending condition being substantially equal in magnitude and substantially opposite in direction relative to the first bending condition, wherein applying the second bending moment to the beam includes applying opposing separation forces on the first and second rigid arms, the separation forces being generally parallel with the longitudinal axis of the beam and opposite the compressive forces;
   wherein applying the first and second bending moments to the beam are performed without changing the rotational orientation of the beam relative to the testing apparatus.

12. The method of claim 11, wherein applying the first and second bending moments to the beam comprises causing the beam to vibrate such that the intermediate portion of the beam oscillates between the first and second bending conditions.

13. The method of claim 11, wherein applying the first and second bending moments to the beam comprises applying equal and opposite bending moments to respective first and second end portions of the beam.

14. The method of claim 13, wherein positioning the beam in the testing apparatus comprises coupling the first end portion of the beam to a first portion of the apparatus that is configured to apply the first bending moment to the first end portion of the beam and coupling the second end portion of the beam to second portion of the apparatus that is configured to apply the second bending moment to the second end portion of the beam.

15. The method of claim 14, wherein applying the first bending moment to the first end portion of the beam comprises applying a first variable pressure distribution along a first side of the first end portion of the beam and applying a second variable pressure distribution along a second side of the first end portion of the beam.

* * * * *